US012774320B2

(12) United States Patent
Quinn et al.

(10) Patent No.: US 12,774,320 B2
(45) Date of Patent: Oct. 27, 2026

(54) SPECIFIC DETECTION OF CLUSTERIN ISOFORMS

(71) Applicant: IDEXX Laboratories, Inc., Westbrook, ME (US)

(72) Inventors: John Joseph Quinn, Falmouth, MA (US); Murthy VSN Yerramilli, Falmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 679 days.

(21) Appl. No.: 15/568,653

(22) PCT Filed: Apr. 29, 2016

(86) PCT No.: PCT/US2016/030075

§ 371 (c)(1),
(2) Date: Oct. 23, 2017

(87) PCT Pub. No.: WO2016/176565

PCT Pub. Date: Nov. 3, 2016

(65) Prior Publication Data

US 2018/0142009 A1 May 24, 2018

Related U.S. Application Data

(60) Provisional application No. 62/155,175, filed on Apr. 30, 2015.

(51) Int. Cl.

| | |
|---|---|
| ***C07K 16/18*** | (2006.01) |
| ***G01N 33/52*** | (2006.01) |
| ***G01N 33/533*** | (2006.01) |
| ***G01N 33/534*** | (2006.01) |
| ***G01N 33/535*** | (2006.01) |
| ***G01N 33/543*** | (2006.01) |
| ***G01N 33/68*** | (2006.01) |

(52) U.S. Cl.

CPC ........... *C07K 16/18* (2013.01); *G01N 33/523* (2013.01); *G01N 33/533* (2013.01); *G01N 33/534* (2013.01); *G01N 33/535* (2013.01); *G01N 33/54326* (2013.01); *G01N 33/54386* (2013.01); *G01N 33/68* (2013.01); *G01N 33/6893* (2013.01); *G01N 2333/775* (2013.01); *G01N 2800/347* (2013.01)

(58) Field of Classification Search

CPC ...... C07K 16/18; G01N 33/68; G01N 33/523; G01N 33/533; G01N 33/534; G01N 33/535; G01N 33/54326; G01N 33/54386; G01N 33/6893; G01N 2333/775; G01N 2800/347; G01N 2333/42

See application file for complete search history.

(56) References Cited

U.S. PATENT DOCUMENTS

| | | | | |
|---|---|---|---|---|
| 2007/0178538 | A1* | 8/2007 | Haab ................ | G01N 33/57438 435/7.23 |
| 2012/0282251 | A1 | 11/2012 | Tremblay et al. | |
| 2012/0283129 | A1 | 11/2012 | Al-Murrani et al. | |
| 2017/0233487 | A1 | 8/2017 | Tremblay et al. | |

FOREIGN PATENT DOCUMENTS

| | | | |
|---|---|---|---|
| BR | 1120170167 | A2 | 7/2018 |
| BR | 11017021946 | A2 | 7/2018 |
| BR | 112017021645 | A2 | 7/2018 |
| BR | 112017021670 | A2 | 7/2018 |
| BR | 112017021850 | A2 | 7/2018 |
| BR | 112017022021 | A2 | 7/2018 |
| JP | 2714664 | B2 * | 2/1998 |
| JP | 2008541060 | A | 11/2008 |
| JP | 6948265 | B2 | 10/2021 |
| WO | 2004005934 | A2 | 1/2004 |
| WO | 2006121892 | A2 | 11/2006 |
| WO | 2010132447 | A2 | 11/2010 |
| WO | 2012102963 | A1 | 8/2012 |
| WO | 2014197729 | A1 | 12/2014 |
| WO | 2016176565 | A1 | 11/2016 |

OTHER PUBLICATIONS

Blaschuk et al (J. Biol Chem 1983, vol. 258 No. 12 issue 25 pp. 7714-7720).*
Okura et al (J. Biochem 2002;891-901).*
Kuno et al (Mol. Cel. Proteomics 2009, p. 99-108).*
Lamoureux et al (Journal of toxicology and environmental health 2011;74:138-145).*
Chen et al. (Nature Methods 2007; vol. 4 No. 5, pp. 438-444).*
Wu et al., Altered Expression of Sialyated Glycoproteins in Ovarian Cancer Sera Using Lectin-based ELISA Assay and Quantitative Glycoproteomics Analysis, J. Proteome Res. 12, (2013), p. 3342-3352 (Year: 2013).*
Parasuraman et al., Insights into the binding specificity of wild type and mutated wheat germ agglutinin towards Neu5Acα(2-3)Gal: a study by in silico mutations and molecular dynamics simulations, Journal of Molecular Recognition, 27, (2014), p. 482-492 (Year: 2014).*
Aulitzky, et al., Measurement of urinary clusterin as an index of nephrotoxicity. (1992) Proc Soc Exp Biol Med 199 : p. 93-96 (Year: 1992).*
Dieterle et al., Urinary clusterin, cystatin C, β2-microglobulin and total protein as markers to detect drug-induced kidney injury, Nature Biotechnology, 28(5), (2010), p. 463-472 (Year: 2010).*
Mazhari et al., Hematuria: An algorithmic approach to finding the cause, Cleveland Clinic Journal of Medicine, 69(11), (2002), p. 870-884. (Year: 2002).*
Janiszewska et al., The influence of clusterin glycosylation variability on selected pathophysiological processes in the human body, Oxidative Medicine and Cellular Longevity, 2022, (2022) (25 pages) (Year: 2022).*

(Continued)

*Primary Examiner* — Ellen J Marcsisin
(74) *Attorney, Agent, or Firm* — Lathrop GPM LLP; Lisa Hillman

(57) ABSTRACT

The invention provides methods and compositions for the detection of specific isoforms of clusterin.

21 Claims, 9 Drawing Sheets

(56) References Cited

OTHER PUBLICATIONS

Linda Ross, Acute Kidney Injury in Dogs and Cats, Veterinary Clinics of North America: Small Animal Practice, 41(1), (2011), pp. 1-14 (Year: 2011).*

Sondej et al., Glycoprofiling of the Human Salivary Proteome, Clin. Proteomics, 5(1), (2009), p. 52-68. (Year: 2009).*

Moreno et al., Haematuria: the forgotten CKD factor?, Nephrol Dial. Transplant, 27, (2012), p. 28-34. (Year: 2012).*

Kapron et al., "Identification and characterization of glycosylation sites in human serum clusterin", Protein Science, 6(10):2120-2133 (1997).

International Search Report for corresponding PCT application No. PCT/US2016/030075, dated Jul. 4, 2016.

Kapron, James T. et al., Identification of glycosylation sites in human serum clusterin. Protein Science, v. 6, b. 10, p. 2120-2133, 1997 https://onlinelibrary.wilely.com/doi/abs/10.1002/pro/5560061007.

Office Action Issued in Brazilian Application No. 112017021850-0 dated Oct. 8, 2019, 5 pages.

NZ Application No. 736200, Patent examination report 1, dated Feb. 19, 2021, 5 pages.

Wilson et al, "Clusterin enhances the formulation of insoluble immune complexes", Biochem Biophys Commun, vol. 177, No. 3, pp. 985-990, Jun. 28, 1991.

Chen et al, "Mass spectrometry quantification of clusterin in the human brain", Molecular Neurodegeneration, 7:41, (2012).

Cowgill et al, "Is Progressive Chronic Kidney Disease a Slow Acute Kidney Injury?". Vet Clin Small Anim, vol. 46, pp. 995-1013, (2016).

Faraggiana et al, "Lectin-peroxidase conjugate reactivity in normal human kidney.", Journal of Histochemistry & Cytochemistry, 30:451, (1982).

French et al, "Clusterin in renal tissue: preferential localization with the terminal complement complex and immunoglobulin deposits in glomeruli", Clin. Exp. Immunol., vol. 88, pp. 389-393, (1992).

Garcia-Martinez et al, "Urinary clusterin as a renal marker in dogs", Journal of Veterinary Diagnostic Investigation, vol. 24, No. 2, pp. 301-306, (2012).

Ghiggeri et al, "Depletion of clusterin in renal diseases causing nephrotic syndrome", Kidney International, vol. 62, pp. 2184-2194, (2002).

Hara-Kuge et al, "Involvement of VIP36 in Intracellular Transport and Secretion of Glycoproteins in Polarized Madin-Darby Canine Kidney (MDCK) Cells", J. Boil. Chem, vol. 277, pp. 16332-16339, (2002).

Hidaka et al, "Urinary clusterin levels in the rat correlate with the severity of tubular damage and may help to differentiate between glomerular and tubular injuries", Cell Tissue Res, vol. 310, pp. 289-296, (2002).

Holthöfer, "Lectin binding sties in kidney . A comparative study of 14 animal species", Journal of Histochemistry & Cytochemistry, 31: 531, (1983).

Jung et al, "Clusterin Attenuates the Development of Renal Fibrosis", J Am Soc Nephrol, vol. 23, pp. 73-85, (2012).

Khan et al, "Study of Renal Tubular Glycoconjugates in Tubulointerstitial Damage Using Conjugated Lectins", Journal of Pathology, vol. 170, pp. 187-196, (1993).

Kovak et al, "Proteomic identification of galectin-3 binding ligands and characterization of galectin-3 proteolytic cleavage in human prostasomes", Andrology, vol. 1, pp. 682-691, (2013).

Kratz et al, "Glycosylation Changes in the Salivary Glycoproteins of Alcohol-Dependent Patients: A Pilot Study", Alcohol and Alcoholism, vol. 49, No. 1, pp. 23-30, (2014).

Mares et al, "Specific adsorption of some complement activation proteins to polysulfone dialysis membranes during hemodialysis", Kidney International, vol. 76, pp. 404-413, (2009).

Mu et al, "Identification of O-glycosylated Proteins That Are Aberrantly Excreted in the Urine of Patients with Early Stage Ovarian Cancer", In. J. Mol. Sci., vol. 14, pp. 7923-7931, (2013).

Murata et al, "Distribution of Glycoconjugates in the Kidney Studied by Use of Labeled Lectins", The Journal of Histochemistry and Cytochemistry, vol. 31, No. 1A, pp. 139-144, (1983).

Prochnow et al, "Non-Secreted Clusterin Isoforms Are Translated in Rare Amounts from Distinct Human mRNA Variant and Do Not Affect Bax-Mediated Apoptosis of the NF-kB Signaling Pathway", PLOS ONE, vol. 8, No. 9, e75303, Sep. 2013.

Sabatte et al, "Semen Clusterin Is a Novel DC_SIGN Ligand", J Immunol, vol. 187, pp. 5299-5309, Oct. 17, 2011.

Tsuchiya et al, "Investigation on urinary proteins and renal mRNA expression in canine renal papillary necrosis induced by nefiracetam", Arch Toxicol, vol. 79, pp. 500-507, (2005).

Vaidya et al, "Biomarkers of Acute Kidney Injury", Annu Rev Pharmacol Toxcol, vol. 48, pp. 463-493, (2008).

Wu et al, "Altered Expression of Sialylated Glyoproteins in Ovarian Cancer Sera Using Lectin-based ELISA Assay and Quantitative Glycoproteomics Analysis", J. Proteome Res, vol. 12, pp. 3342-3352 (2013).

Yerramilli et al, "Kidney Disease and the Nexus of Chronic Kidney Disease and Acute Kidney Injury; The Role of Novel Biomarkers as Early and Accurate Diagnostics", Vet Clin Small Anim, (2016).

Zhou et al, "Evaluation of the usefulness of novel biomarkers for drug-induced acute kidney injury in beagle dogs", Toxicology and Applied Pharmacology, vol. 280, pp. 30-35, (2014).

Slide presentation by Larry D. Cowgill, DMV, PhD, "Application of Novel Kidney Biomarkers in Urinary Tract Infection", Department of Medicine & Epidemiology, University of California, Davis in collaboration with Murthy Yerramilli of IDEXX and Shelly Vaden of N.C. State University, (2016).

Slide presentation by Murthy Yerramilli, Ph.D., Senior Director, R&D, "Novel Kidney Biomarkers: Discovery & Future", IDEXX Laboratories, Mar. 2016.

Dvergten et al, "Expression of clusterin in human renal diseases", Kidney International, vol. 45, pp. 828-835, (1994).

Mu et al, "Identification of O-glycosylated Proteins That Are Aberrantly Excreted in the Urine of Patients With Early Stage Ovarian Cancer", Int. J. Mol. Sci., vol. 12, pp. 7923-7931, (2013).

Japanese Patent Application No. 2017-556249, Office Action, dated Mar. 18, 2020, 5 pages.

* cited by examiner

| Dilution Serum: Negative Urine | Clusterin (ng/ml) |
|---|---|
| 1:10 | 4869 |
| 1:20 | 2597 |
| 1:50 | 1142 |
| 1:100 | 623 |
| 1:500 | 113 |
| 1:1000 | 62 |
| 1:5000 | 23 |
| 0 | 13 |

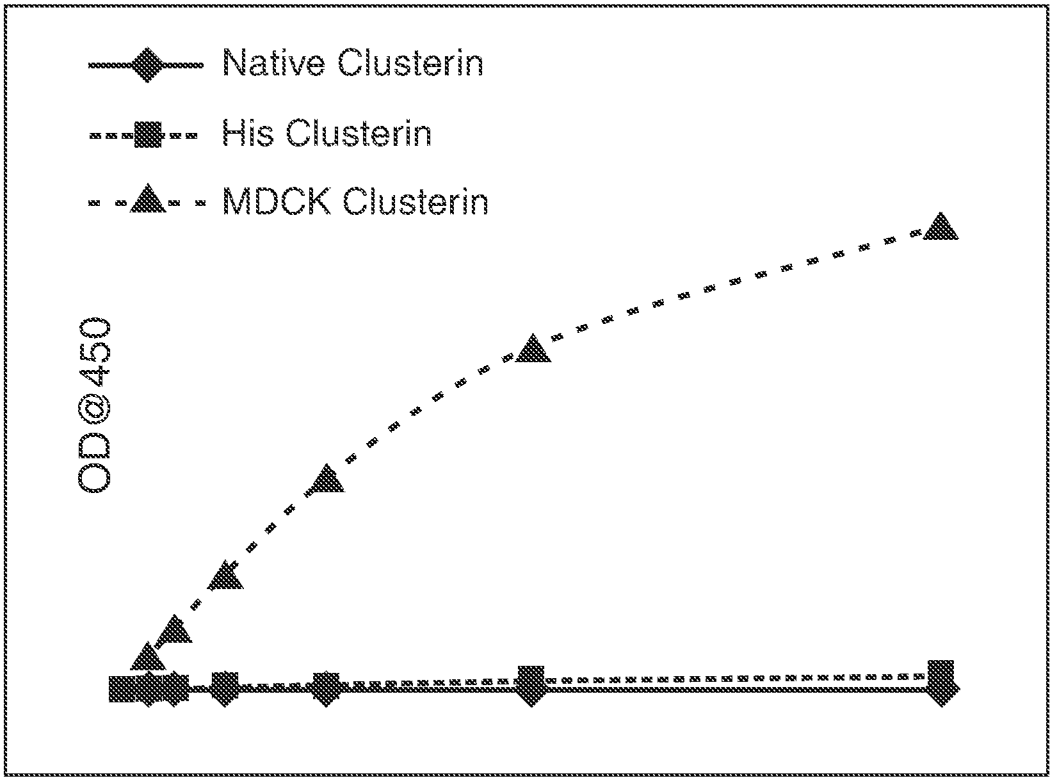
Figure 2: Binding of clusterin to lectin solid phase

1. MWM Marker
2. MDCK Sup
3 HEK293 Sup
4. MDCK Clusterin
5. rBeta Chain Clusterin

SPECIFIC DETECTION OF CLUSTERIN ISOFORMS

PRIORITY

This application claims the benefit of U.S. Ser. No. 62/155,175, filed on Apr. 30, 2015, which is incorporated by reference in its entirety herein.

BACKGROUND OF THE INVENTION

Clusterin or Apolipoprotein J is a 75-80 kDa disulphide linked heterodimeric protein. Clusterin is part of many physiological processes including sperm maturation, lipid transportation, complement inhibition, tissue remodeling, membrane recycling, stabilization of stressed proteins, and promotion of inhibition of apoptosis. Clusterin is over-expressed during kidney proximal and distal tubular damage, has been noticed in various carcinomas, and is up-regulated in kidney injury.

There are several immunoassays that have been developed and marketed for measuring clusterin in various body fluids including plasma, serum, and urine. Kidney specific clusterin can be used as a marker of kidney damage or disease. However, contamination of urine samples with blood is a commonly observed occurrence due to infection, trauma, neoplasia, inflammation, and accidental contamination during catherization and cystocentisis. This is more profound problem in veterinary medicine. In healthy populations serum concentrations of clusterin are 1000-fold higher (60-100 μg/ml) than the concentrations in urine (<100 ng/ml). The blood contamination brings non-kidney specific clusterin isoforms into the urine. Hence, it is important to ensure that the quantification of kidney specific clusterin isoform is not impacted by contamination of serum clusterin from the blood. Failure to do so can result in false positive test results in urine clusterin assays. Methods are needed in the art to differentiate clusterin isoforms in bodily samples.

SUMMARY OF THE INVENTION

The invention provides methods of specifically detecting a first clusterin isoform. The methods comprise contacting a sample with one or more antibodies or antigen binding fragments thereof that specifically bind clusterin and one or more molecules that specifically bind to carbohydrate moieties of the first clusterin isoform and that do not specifically bind to carbohydrate moieties of other clusterin isoforms. Complexes of the first clusterin, the one or more antibodies or antigen binding fragments thereof that specifically bind clusterin, and the one or more molecules that specifically bind to carbohydrate moieties of the first clusterin and that do not specifically bind to carbohydrate moieties of other clusterin isoforms are detected.

The invention also provides methods of detecting kidney specific clusterin. The methods comprise contacting a sample with one or more antibodies or antigen binding fragments thereof that specifically bind clusterin and one or more molecules that specifically bind to carbohydrate moieties of kidney specific clusterin and that do not specifically bind to carbohydrate moieties of other clusterin isoforms (e.g., plasma clusterin, serum clusterin, or bloodborne, non-kidney specific clusterin). Complexes of kidney specific clusterin, the one or more antibodies or antigen binding fragments thereof that specifically bind clusterin, and the one or more molecules that specifically bind to carbohydrate moieties of kidney specific clusterin and that do not specifically bind to carbohydrate moieties of other clusterin isoforms are detected. The one or more molecules that specifically bind to carbohydrate moieties of kidney specific clusterin and that do not specifically bind to carbohydrate moieties of other clusterin isoforms (e.g., plasma clusterin, serum clusterin, or bloodborne, non-kidney specific clusterin), can be one or more lectins or one or more molecules that specifically bind N-acetylglucosamine. The one or more lectins can be lectins that specifically bind N-acetylglucosamine. Lectins can be *Phaseolus vulgaris* leucoagglutanin (PHA-L), wheat germ agglutinin (WGA), WGA1, WGA2, WGA3, sWGA, *Phaseolus vulgaris* agglutinin-E (PHA-E), *Lycopersicon esculentum* lectin (LEL), *Datura stramonium* lectin (DSL), *Pisum sativum* agglutinin (PSA), or *Dolichos biflorus* lectin (DBA).

The one or more antibodies or antigen binding fragments thereof can be immobilized to a support. The sample and detectably labeled one or more molecules that specifically bind to carbohydrate moieties of kidney specific clusterin and that do not specifically bind to carbohydrate moieties of other clusterin isoforms (which can be lectins) can be added to the support.

The one or more molecules that specifically bind to carbohydrate moieties of kidney specific clusterin and that do not specifically bind to carbohydrate moieties of other clusterin isoforms (which can be lectins) can be immobilized to a support. The sample and detectably labeled one or more antibodies or antigen binding fragments thereof can be added to the support.

The one or more antibodies or antigen binding fragments thereof, the one or more molecules that specifically bind to carbohydrate moieties of kidney specific clusterin and do not bind to carbohydrate moieties of other clusterin isoforms (e.g., plasma clusterin, serum clusterin, or bloodborne, non-kidney specific clusterin), or both can be labeled with a detectable label.

The one or more lectins can be lectins that do not specifically bind serum and plasma clusterin. The sample can be a urine sample. The detection can be completed by a method selected from the group consisting of a lateral flow assay, a chemiluminescent labeled sandwich assay, and an enzyme-linked immunosorbant assay (ELISA), a competitive assay, an agglutination assay, a chemiluminescent assay, a bioluminescent assay, a gel electrophoresis immunoassay method, an immunohistochemistry assay, a radioimmunoassay (RIA), a label-free biosensor assay, or an immunoradiometric assay. The antibodies can specifically bind plasma clusterin, serum clusterin, recombinant clusterin, kidney specific clusterin, or MDCK-derived clusterin. The kidney specific clusterin can be human, feline, or canine.

Other embodiments of the invention provide methods for detecting kidney disease, kidney injury, or kidney damage in a mammal. The methods comprise contacting a sample from a mammal with one or more antibodies or antigen binding fragments thereof that specifically bind clusterin and one or more molecules that specifically bind to carbohydrate moieties of kidney specific clusterin and that do not specifically bind to carbohydrate moieties of other clusterin isoforms (e.g., plasma clusterin, serum clusterin, or bloodborne, non-kidney specific clusterin). Complexes of kidney specific clusterin, one or more antibodies or antigen binding fragments thereof that specifically bind clusterin and one or more molecules that specifically bind to carbohydrate moieties of kidney specific clusterin and that do not specifically bind to carbohydrate moieties of other clusterin isoforms are detected. If the complexes are detected, then the mammal has kidney disease, kidney injury, or kidney damage. A kidney therapy or kidney therapeutic can be administered to the mammal if the mammal has kidney disease, kidney damage, or kidney injury. The kidney disease can be a urinary tract infection. The mammal can be a human, feline, or canine.

Other embodiments of the invention provide methods of distinguishing one more clusterin isoforms from other types of clusterin isoforms. The methods comprise contacting a sample with one or more antibodies or antigen binding fragments thereof that specifically bind clusterin and one or more molecules that specifically bind to carbohydrate moieties of the one or more clusterin isoforms and do not bind to carbohydrate moieties of the other clusterin isoforms. Complexes of the one or more isoforms of clusterin, one or more antibodies or antigen binding fragments thereof that specifically bind clusterin, and the one or more molecules that specifically bind to carbohydrate moieties of the one or more clusterin isoforms and that do not bind to carbohydrate moieties of the other clusterin isoforms are detected. The one or more clusterin isoforms can be kidney specific clusterin and the other clusterin isoforms can be, e.g., plasma clusterin, serum clusterin, or bloodborne, non-kidney specific clusterin. The one or more clusterin isoforms can be human, feline, or canine clusterin isoforms.

Other embodiments of the invention provide a complex comprising one or more clusterin molecules, one or more antibodies or antigen binding fragments thereof that specifically bind clusterin, and one or more lectins. The complex can comprise one or more kidney specific clusterin molecules, one or more antibodies or antigen binding fragments thereof that specifically bind clusterin, and one or more molecules that specifically bind to carbohydrate moieties of kidney specific clusterin and that do not bind to carbohydrate moieties of other clusterin isoforms (e.g., plasma clusterin, serum clusterin, or bloodborne, non-kidney specific clusterin). The complex can be immobilized to any type of solid support. The complex can additionally comprise one or more detectable labels, which can be associated with one or more of the molecules of the complex.

Other embodiments of the invention provide a kit comprising one or more antibodies or antigen binding fragments thereof that specifically bind clusterin and one or more the one or more molecules that specifically bind to carbohydrate moieties of kidney specific clusterin and that do not bind to carbohydrate moieties of other clusterin isoforms (e.g., plasma clusterin, serum clusterin, or bloodborne, non-kidney specific clusterin). The one or more antibodies or antigen binding fragments thereof, the one or more molecules that specifically bind to carbohydrate moieties of kidney specific clusterin and that do not bind to carbohydrate moieties of other clusterin isoforms, or both are labeled with a detectable label. The detectable label can be an enzyme, an enzyme conjugate, a fluorescent compound, a chemiluminescent compound, a radioactive element, a direct visual label, or a magnetic particle.

Other embodiments of the invention provide a method of improving detection of clusterin and clusterin isoforms. The methods comprise contacting a sample with one or more clusterin antibodies or specific binding fragments thereof and one or more molecules that specifically bind to one or more carbohydrate moieties of clusterin. Complexes of one or more clusterin antibodies or specific binding fragments thereof and one or more molecules that specifically bind to one or more carbohydrate moieties of clusterin are detected with improved sensitivity, specificity, or both.

Therefore, the instant invention provides methods and compositions for the detection and/or quantification of a first specific clusterin isoform, optionally in the presence of one or more second clusterin isoforms, such that the one or more second clusterin isoforms do not significantly interfere with the detection and/or quantification of the first specific clusterin isoform.

BRIEF DESCRIPTION OF THE DRAWINGS

FIG. 2 shows binding of clusterin to a lectin solid phase.

DETAILED DESCRIPTION OF THE INVENTION

Figures 1A, 1B:
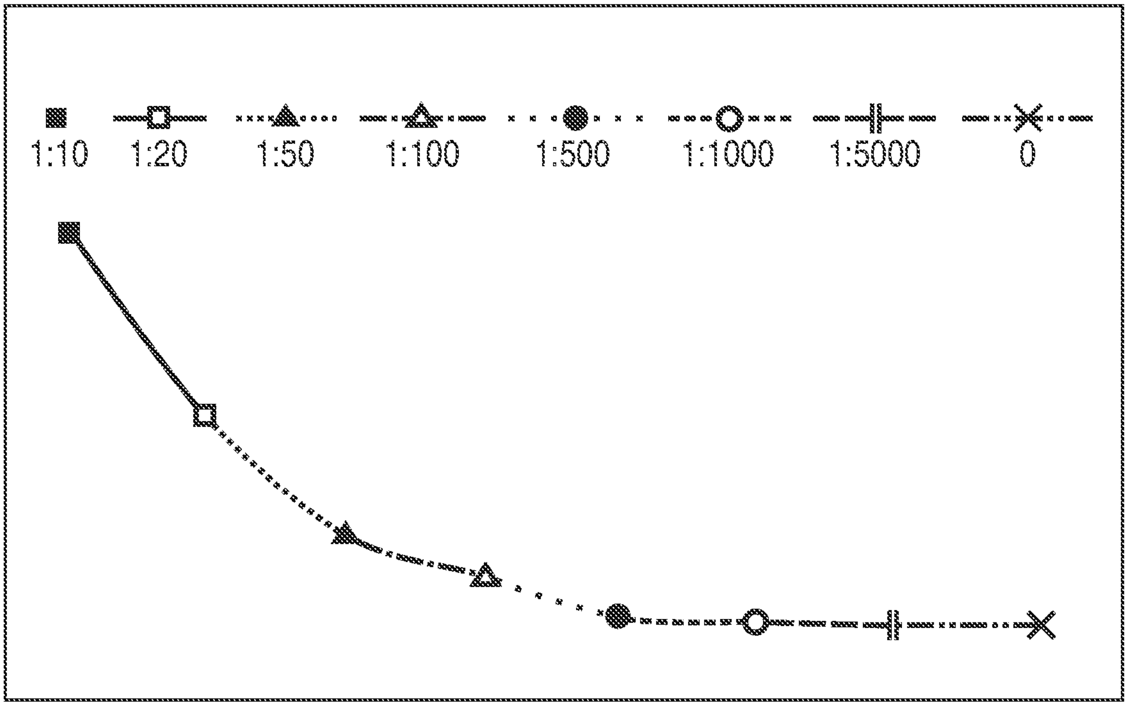
FIG. 1A-B show clusterin levels in normal (i.e., healthy) canine urine that was spiked with varying dilutions of normal canine serum.

As used herein, the singular forms "a," "an," and "the" include plural referents unless the context clearly dictates otherwise. The term "about" in association with a numerical value means that the numerical value can vary plus or minus by 5% or less of the numerical value.

Kidney specific clusterin is an acute kidney injury (AKI) biomarker that increases during and, as a result of, kidney injury in mammals such as dogs, cats, and humans. A commercial EIA kit from Biovendor is available for the quantification of canine clusterin in both serum and urine. A recent study validated the biomarker using this kit in dogs with leishmaniasis. However, contamination of urine samples with serum can provide false positive results due to the high concentration of clusterin in serum. The contamination of urine samples with blood results in the lack of specificity in the detection of kidney specific clusterin due to the contamination by serum clusterin.

To demonstrate the complications of false positives from general total clusterin measurements a negative canine urine sample was value assigned using a commercial kit (Biovendor) and then spiked with negative canine serum (0.002% to 10% v/v). The resulting mixtures were analyzed using the commercial kit and the results obtained are shown in the table below:

TABLE 1

| Sample | % Contamination | Observed [kidney specific clusterin] ng/ml |
|---|---|---|
| Neat Negative Urine | 0 | 13 |
| Urine + 10% Serum | 10 | 4869 |
| Urine + 5% Serum | 5 | 2587 |
| Urine + 2% Serum | 1 | 1142 |
| Urine + 1% Serum | 0.5 | 623 |
| Urine + 0.2% Serum | 0.1 | 113 |
| Urine + 0.01% Serum | 0.05 | 62 |
| Urine + 0.002% Serum | 0.001 | 23 |

The commercial cut off is about 70 ng/ml. When the total clusterin is measured (all isoforms), even minute amounts of blood, which are not visible to the naked eye or detectable by conventional urinalysis (dipstick) can cause false positives. This means that the patient samples that have any hint of blood contamination have to be evaluated very carefully since the possibility of false positives leading to false clinical diagnoses is increased. The instant invention provides methods of identifying specific isoforms of clusterin in bodily fluids, for example, the determination of presence and/or quantity of kidney specific clusterin with no interference by serum clusterin. That is, the instant invention can be used to detect and/or quantify specific clusterin isoforms, e.g. kidney specific clusterin in the presence of other clusterin isoforms.

The primary structures of all clusterin isoforms are highly homologous. However, it was thought that there would be differences in the post-translational modification patterns between various clusterin isoforms. The specific oligosaccharide structures on clusterin isoforms are associated with tissue source, physiological status, disease state, and species. The methods of the instant invention take advantage of these differences in developing detection methods for specific clusterin isoforms (e.g., kidney injury specific clusterin isoforms) that are present in patient samples (e.g., urine samples).

Clusterin Isoforms

"Clusterin isoforms" as used herein, are clusterin molecules that are a product of a gene splicing or duplication event, which are glycosylated (see, e.g., Rizzi et al., Adv. Cancer Res. 104:9 (2009); Prochnow et al., PLOS One, 8:e75303 (2013)). Clusterin isoforms include nuclear, cytoplasmic, and secreted forms. A "clusterin isoform" also comprises clusterin glycoforms, which are forms of clusterin that are differentially glycosylated due to, e.g., expression in a specific tissue type, expression in a specific physiological state, expression in a specific species type, expression in a specific disease state, or under conditions of cell damage.

"Kidney specific clusterin" or "kidney specific clusterin isoform" is clusterin produced in the renal system (i.e., kidneys, ureters, urethra, and the bladder) that can be present in the renal system, including urine. Small amounts of kidney specific clusterin, however, can leak into blood, serum, or plasma. Increased levels of kidney specific clusterin can be present in the renal system, including urine, of animals and humans with kidney injury, kidney damage, and/or kidney disease as compared to animals and humans with no kidney injury, kidney damage, and/or kidney disease.

"Serum clusterin" and "plasma clusterin" are clusterin isoforms that are synthesized in tissues such as heart, liver and lung that are released into circulation in blood, plasma, or fractions thereof. "Serum clusterin" and "plasma clusterin" do not include kidney specific clusterin that originated in the renal system or kidney specific clusterin that originated in the renal system and then leaked into circulating blood, serum, plasma, or fractions thereof. Non-kidney specific clusterin isoforms are those clusterin isoforms that are not produced in the renal system (e.g., serum or plasma clusterin). Bloodborne clusterin isoforms are those that are present in circulating blood, plasma, serum or fractions thereof.

Secreted clusterin is produced from an initial protein precursor, presecretory psCLU (~60 kDa), heavily glycosylated, and then cleaved in the endoplasmic reticulum (ER). The resulting alpha- and beta-peptide chains are held together by 5 disulfide bonds in the mature secreted heterodimer protein form (~75-80 kDa).

The glycosylation of clusterin can be different for different isoforms of clusterin. For example, kidney specific clusterin and serum or plasma clusterin can have different glycosylation patterns. This difference in glycosylation between isoforms of clusterin can be used to differentiate one isoform of clusterin from other isoforms of clusterin.

Clusterin isoforms can be differentiated in, for example, mammals, humans, canines, felines, equines, bovines, ovines, simians, and other animals using the methods of the invention. Differentiation includes, for example, determining the presence or absence of a first clusterin isoform in the presence of one or more second types of clusterin isoforms.

Antibodies

Antibodies of the invention are antibody molecules or antigen binding fragments thereof that specifically bind to clusterin. The antibodies or antigen binding fragments thereof can be specific for human, canine, feline, equine, bovine, ovine, or simian clusterin. The antibodies or antigen binding fragments thereof can be specific for any type of clusterin isoform (e.g., kidney specific clusterin, plasma clusterin, or serum clusterin). In embodiments of the invention, an antibody or antigen binding fragment thereof specifically binds kidney specific clusterin. In other embodiments an antibody or antigen binding fragment thereof specifically binds one or more isoforms of clusterin, all isoforms of clusterin, serum clusterin, or plasma clusterin. An antibody of the invention can be a polyclonal antibody, a monoclonal antibody, a single chain antibody (scFv), a bispecific antibody, a multispecific antibody, a chimeric antibody, a monovalent antibody, a bivalent antibody, a multivalent antibody, an anti-idiotypic antibody, or an antigen or specific binding fragment of an antibody. An antigen binding fragments or specific binding fragment of an antibody is a portion of an intact antibody comprising the antigen binding site or variable region of an intact antibody. Examples of antigen binding antibody fragments include Fab, Fab', Fab'-SH, $F(ab')_2$, Fd, single chain Fvs (scFv), disulfide-linked Fvs (sdFv), fragments comprising a $V_L$ or a $V_H$ domain or a $V_L$ domain and a $V_H$ domain, and $F_v$ fragments.

An antibody of the invention can be any antibody class, including for example, IgG (IgG1, IgG2a, IgG2b, IgG3, IgG4), IgM, IgA (IgA1, IgA2), IgD and IgE. An antibody or antigen binding fragment thereof binds to one or more epitopes of a clusterin molecule, such as a kidney specific clusterin molecule, a plasma clusterin molecule, or a serum clusterin molecule. An antibody can be made in vivo in suitable laboratory animals or in vitro using recombinant DNA techniques. Means for preparing and characterizing antibodies are well known in the art. See, e.g., Dean, *Methods Mol. Biol.* 80:23-37 (1998); Dean, *Methods Mol. Biol.* 32:361-79 (1994); Baileg, *Methods Mol. Biol.* 32:381-

88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a clusterin molecule or part of a clusterin molecule to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds" or "specific for" means that a first antigen, e.g., a clusterin or a portion thereof, recognizes and binds to an antibody or antigen binding fragment thereof with greater affinity than other non-specific molecules. A non-specific molecule is an antigen that shares no common epitope with the first antigen. In embodiments of the invention a non-specific molecule is not a clusterin isoform and is not related to clusterin. For example, an antibody raised against a first antigen (e.g., a clusterin molecule) to which it binds more efficiently than to a non-specific antigen can be described as specifically binding to the first antigen. In embodiments of the invention, an antibody or antigen-binding fragment thereof specifically binds to a clusterin molecule or portion thereof when it binds with a binding affinity $K_a$ of $10^7$ l/mol or more. In the instant invention an antibody or antigen binding fragment can specifically bind to 2 or more isoforms of clusterin or can specifically bind to only one isoform of clusterin, e.g., kidney specific clusterin. Specific binding can be tested using, for example, an enzyme-linked immunosorbant assay (ELISA), a radioimmunoassay (RIA), or a western blot assay using methodology well known in the art.

Antibodies of the invention can be chimeric (see, e.g., U.S. Pat. No. 5,482,856), humanized (see, e.g., Jones et al., *Nature* 321:522 (1986); Reichmann et al., *Nature* 332:323 (1988); *Presta, Curr. Op. Struct. Biol.* 2:593 (1992)), caninized, canine, or human antibodies. Human antibodies can be made by, for example, direct immortilization, phage display, transgenic mice, or a Trimera methodology, see e.g., Reisener et al., *Trends Biotechnol.* 16:242-246 (1998).

An assay for detection of a clusterin molecule can utilize one antibody or antigen binding fragment thereof or one or more antibodies or fragments (e.g., 1, 2, 3, 4, 5, 10 or more antibodies). An assay for clusterin can use, for example, a monoclonal antibody specific for a clusterin epitope, a combination of monoclonal antibodies specific for epitopes of one clusterin molecule, monoclonal antibodies specific for epitopes of different clusterins, polyclonal antibodies specific for the same clusterin epitope, polyclonal antibodies specific for different clusterin epitopes, or a combination of monoclonal and polyclonal antibodies. Assay protocols can be based upon, for example, competition, direct reaction, or sandwich type assays using, for example, labeled antibody.

Antibodies of the invention can be labeled with any type of label known in the art, including, for example, fluorescent, chemiluminescent, radioactive, enzyme, colloidal metal, radioisotope, and bioluminescent labels.

Antibodies that specifically bind clusterin include, for example, 9H7, 3A4, 2F2, antibodies specific for the alpha chain of clusterin, antibodies specific for the beta chain of clusterin, anti-clusterin urine isoform, Hs-3; 3R3-2; CLI-9; 1A11; 2F12; A4; 7D1; 3R3/2, clusterin C-Term antibody, clusterin isoform I antibody, CLU (AA 1-333)(N-Term) antibody, CLU N-Term (AA 79-99) antibody, CLU (AA 312-325) antibody, CLU (AA 44-58) antibody, CLU (AA 402-501) antibody, CLU (AA 75-501) antibody, CLU (AA 312-325) antibody; antibody LS-B6759, antibody LS-B3762, antibody LS-B2937, and LS-B2852, antibody 16B5. An antibody can specifically bind kidney specific clusterin or both kidney specific clusterin and other forms of clusterin (e.g., serum or plasma clusterin).

Lectins

Lectins are proteins that recognize and bind specific monosaccharide or oligosaccharide structures (carbohydrates). A lectin usually contains two or more binding sites for carbohydrate units. The carbohydrate-binding specificity of a certain lectin is determined by the amino acid residues that bind the carbohydrate. The binding strength of lectins to carbohydrates can increase with the number of molecular interactions. The dissociation constant for binding of lectins to carbohydrates is about $K_d$ of $10^{-5}$ to $10^{-7}$. "Specifically binds" or "specific for" means that a first lectin, e.g., WGA, recognizes and binds to a specific type of carbohydrate (e.g., N-acetylglucosamine for WGA) with greater affinity than for other non-specific types of carbohydrates. The specific type of carbohydrate is associated with a specific clusterin isoform (e.g., kidney specific clusterin or a species specific clusterin) and not significantly associated with one or more other clusterin isoforms (e.g., serum clusterin). For example, a lectin that binds more efficiently to a first specific type of carbohydrate than to a non-specific carbohydrate can be described as specifically binding to the first specific type of carbohydrate. In embodiments of the invention, a lectin binds more efficiently to a first specific type of carbohydrate than to a non-specific carbohydrate when it binds to the first specific type of carbohydrate with a $K_d$ that is lower by about 5, 10, 20, 30, 40, 50, 60% or more when compared to the binding of the non-specific carbohydrate. In embodiments of the invention, a lectin specifically binds to a specific type of carbohydrate when it binds with a dissociation constant $K_d$ of about $10^{-5}$ to $10^{-7}$. In the instant invention a lectin can specifically bind to 2 or more specific types of carbohydrates or can specifically bind to only one specific type of carbohydrate.

Lectins can be labeled with any type of label known in the art, including, for example, fluorescent, chemiluminescent, radioactive, enzyme, colloidal metal, radioisotope and bioluminescent labels.

In embodiments of the invention lectins are used that specifically bind kidney specific clusterin and that do not specifically bind plasma or serum clusterin. In embodiments of the invention lectins that specifically bind N-acetylglucosamine are useful in the invention. Such lectins include, for example, WGA (wheat germ agglutinin), WGA1, WGA2, WGA3, sWGA, DSL lectin (*Datura stramonium* lectin), mannose binding lectin, PHA-L (*Phaseolus vulgaris* leucoagglutanin), PHA-E (*Phaseolus vulgaris* erythoagglutanin), and LEL (*Lycopersicon esculentum* (Tomato) lectin). Other lectins that can be used include, for example jacalin, STL lectin (*Solanum tuberosum*), LCA lectin (*Lens culinaris*), PSA lectin (*Pisum sativum* agglutinin), ECL lectin (*Erythina cristagalli*), RCA lectin (Ricin *communis*), DBA lectin (*Dolichos biflorus*), SBA lectin (soybean), and CONA lectin (concanavlin). Lectins are commercially available from, e.g., Vector Laboratories.

Lectins can be used that specifically bind to carbohydrates on human, canine, feline, equine, bovine, ovine, or simian clusterin isoforms. Lectins can also be used that specifically bind one or more plasma, serum, or kidney clusterin isoforms and that do not bind other clusterin isoforms.

Molecules that Specifically Bind to Carbohydrate Moieties of a First Clusterin Isoform and that do not Specifically Bind to Carbohydrate Moieties of Other Clusterin Isoforms In embodiments of the invention one or more molecules that specifically bind to carbohydrate moieties of a first clusterin isoform (e.g., kidney specific clusterin or a species specific clusterin, e.g., canine, feline, or human kidney specific clusterin) and that do not specifically bind to carbohydrate moieties of other clusterin isoforms can be used in assays of the invention. Other clusterin isoforms can be, for example, serum clusterin or plasma clusterin. In an example, the one or more molecules that specifically bind to carbohydrate moieties of a kidney specific clusterin isoform and that do not specifically bind to carbohydrate moieties of bloodborne, non-kidney specific clusterin isoforms can be used in assays of the invention. Examples of such molecules include the lectins discussed above and molecules that specifically bind N-acetylglucosamine.

"Specifically binds" or "specific for" means that a first molecule specifically binds to carbohydrate moieties of a first clusterin isoform (e.g., kidney specific clusterin or a species specific clusterin) and does not specifically bind to carbohydrate moieties of one or more other clusterin isoforms. The first molecule recognizes and binds to a specific type of carbohydrate that occurs on a first clusterin isoform and does not significantly occur on one or more second clusterin isoforms (e.g., N-acetylglucosamine for bacterial chitin-binding domain 3 protein, wherein N-acetylglucosamine is a carbohydrate that occurs on kidney specific clusterin isoforms and that does not significantly occur on serum clusterin isoforms) with greater affinity than other non-specific carbohydrates. For example, a first molecule that binds more efficiently to a first specific type of carbohydrate than to a non-specific carbohydrate can be described as specifically binding to the first specific type of carbohydrate.

In embodiments of the invention, a first molecule that specifically binds to carbohydrate moieties of a first clusterin isoform and does not specifically bind to carbohydrate moieties of other clusterin isoforms, binds more efficiently to a first specific type of carbohydrate than to a non-specific carbohydrate when it binds to the first specific type of carbohydrate with a $K_d$ that is lower by about 5, 10, 20, 30, 40, 50, 60% or more when compared to the binding of the to the non-specific carbohydrate. A first molecule that does not specifically bind to carbohydrate moieties of other clusterin isoforms means that the molecule specifically binds via specific carbohydrate moieties of a first clusterin isoform and does not specifically bind to carbohydrate moieties of a second clusterin isoform, such that binding to the first clusterin isoform can detected and/or quantified in the presence of the second clusterin isoform, wherein the presence of the second clusterin isoform does not significantly interfere with the detection and/or quantification of the first clusterin isoform. In embodiments of the invention, a first molecule specifically binds to a specific type of carbohydrate when it binds with a dissociation constant $K_d$ of about $10^{-5}$ to $10^{-7}$. In the instant invention a first molecule can specifically bind to 2 or more specific types of carbohydrates or can specifically bind to only one specific type of carbohydrate.

In embodiments of the invention one or more molecules that bind N-acetylglucosamine can be used to specifically bind to kidney specific clusterin. One or more molecules that bind N-acetylglucosamine include, for example, a wild-type WGA (wheat germ agglutinin), mutated forms of WGA (e.g., WGA1, WGA2, WGA3, see Parasuraman et al. J. Mol. Recognit. (2014) 27:482-92), barley lectin (BL), rice lectin, *Uritica dioica* agglutinin (UDA), hevein, *Phaseolus vulgaris* chitinase (PVC), potato wound-inducible protein 1 (WIN1), potato wound-inducible protein 2 (WIN2), *Solanum tuberosum* chitinase (STC), tobacco chitinase (TC), poplar wound-inducible protein (POP), bacterial N-acetylglucosamine-binding protein A (GbpA) (from, e.g., *Vibrio cholera, Shewanella onedensis, Shewanella baltica, Vibrio fascheri, Vibrio tapetis, Vibrio vulnificus, Yersinia mollaretii, Yersinia aldovae*) CBP70, *Plasmodium falciparum* Pf120, Pf83, and Pf45 GlcNAc-binding proteins, Arsenophonus nasonieae n-acetylglucosamine-binding protein, bacterial chitin-binding domain 3 protein (from, e.g., *Bacillus thuringiensis, Bacillus cereus, Burkholderia ambifaria*), N-acetyl glucosamine chitinase like lectin from *Tamarindus indica*, phloem protein 2 (PP2, PP2-1A1) from *Arabidopsis thaliana, Streptomyces olivaceoviridis* NgcE, urokinase plasminogen activation receptor-associated protein/ENDO180, amelogenin, and attenuated murine cytomegalovirus.

Assays

The methods of the invention can be used to detect clusterin isoforms (e.g., kidney specific clusterin or species specific clusterin, e.g. canine, human or feline kidney specific clusterin) in a test sample, such as a biological sample or a laboratory sample. A test sample can potentially comprise (1) kidney specific clusterin, (2) kidney specific clusterin and serum clusterin, (3) kidney specific clusterin and one or more types of other non-kidney specific clusterin, (4) one or more types of other non-kidney specific clusterin; or (5) no clusterin. A biological sample can include, for example, tissue, urine, blood, serum, plasma, saliva, sputum, feces, cerebrospinal fluid, amniotic fluid, or wound exudate from a mammal such as a horse, bovine, ovine, cat, dog, mouse, rat, simian, or human. The test sample can be untreated, precipitated, fractionated, separated, diluted, concentrated, or purified. In embodiments of the invention kidney specific clusterin leaks into blood, plasma or serum and can be detected therein.

The methods of the invention can be used to improve detection of clusterin and clusterin isoforms by providing assays that use both a clusterin antibody or specific binding fragment thereof combined with a molecule (e.g., a lectin) that specifically binds to one or more carbohydrate moieties of clusterin. The methods comprise contacting a sample with one or more clusterin antibodies or specific binding fragments thereof and one or more molecules that specifically bind to one or more carbohydrate moieties of clusterin. Complexes of one or more clusterin antibodies or specific binding fragments thereof and one or more molecules that specifically bind to one or more carbohydrate moieties of clusterin are detected with improved sensitivity, specificity, or both. The sensitivity or specificity can be improved by about 2, 5, 10, 20, 30, 40, 50% or more.

In certain embodiments, methods of the invention can be used to detect specific clusterin isoforms (e.g., a kidney specific clusterin or species specific clusterin). The methods comprise contacting one or more antibodies or antigen binding fragments thereof that specifically bind clusterin and one or more other molecules that specifically bind kidney specific clusterin (e.g., molecules that specifically bind to carbohydrate moieties of kidney specific clusterin and do not bind to carbohydrate moieties of other clusterin isoforms) with a test sample under conditions that allow complexes of kidney specific clusterin, antibody or antigen binding fragment thereof, and one or more other molecules that specifically bind kidney specific clusterin to form. The complexes are then detected. The presence of complexes indicates the presence of kidney specific clusterin. The absence of complexes indicates the absence of kidney specific clusterin. One of skill in the art is familiar with assays and conditions that are used to detect complex binding. Complexes can comprise, for example, one or more kidney specific clusterin molecules, one or more antibodies that specifically bind clusterin, and one or more other molecules that specifically bind to kidney specific clusterin and that do not specifically bind other isoforms of clusterin. The other forms of clusterin can be, for example, bloodborne, non-kidney specific clusterin isoforms. The amount of the complexes can be determined and can be used to establish the severity of disease.

Assays of the invention can be used to, e.g., distinguish kidney specific clusterin from other types of clusterin isoforms, to detect kidney specific clusterin in a sample, to quantify kidney specific clusterin in a sample, to distinguish one or more clusterin isoforms (e.g., kidney specific clusterin, serum clusterin, plasma clusterin, species specific clusterin isoforms) from other clusterin isoforms, to quantify clusterin isoforms in a sample, or to detect specific clusterin isoforms in a sample.

Embodiments of the invention provide methods of distinguishing one more clusterin isoforms from other types of clusterin isoforms. The methods comprise contacting a sample with one or more antibodies or antigen binding fragments thereof that specifically bind clusterin and one or more molecules that specifically bind to carbohydrate moieties of the one or more clusterin isoforms (e.g. kidney specific clusterin) and do not bind to carbohydrate moieties of the other clusterin isoforms (e.g., plasma clusterin, serum clusterin, or bloodborne, non-kidney specific clusterin isoforms). Complexes comprising the one or more isoforms of clusterin, one or more antibodies or antigen binding fragments thereof that specifically bind clusterin, and the one or more molecules that specifically bind to carbohydrate moieties of the one or more clusterin isoforms and that do not bind to carbohydrate moieties of the other clusterin isoforms are detected. The one or more clusterin isoforms can be mammalian, human, canine, feline, equine, bovine, ovine, or simian clusterin isoforms.

Competitive assays can be used in methods of the invention. For example, one or more antibodies or antigen binding fragments thereof that specifically bind clusterin can be immobilized to a support. Kidney specific clusterin bound to a detectably labeled lectin and a sample treated with an unlabeled lectin that specifically binds kidney specific clusterin are added to the support. The amount of detectably labeled lectin-kidney specific clusterin that is not bound to the one or more antibodies or antigen binding fragments thereof is detected. The amount of detectably labeled lectin-kidney specific clusterin that is not bound to the one or more antibodies or antigen binding fragments is proportional to the amount of kidney specific clusterin in the sample. Alternatively, the detectably labeled lectin-kidney specific clusterin that is not bound to the one or more antibodies or antigen binding fragments is washed away and the remaining detectably labeled lectin-kidney specific clusterin is detected. Alternatively, the assay can begin with one or more lectins that specifically bind a clusterin isoform are immobilized to the support. Kidney specific clusterin bound to one or more detectably labeled antibodies or antigen binding fragments thereof that specifically bind clusterin along with a sample treated with unlabeled antibodies that specifically bind kidney specific clusterin are added to the support. Detection is completed as described above.

Methods of the invention can be used in the diagnosis or detection of kidney disease, kidney injury, or kidney damage by obtaining a test sample from, e.g., a human or mammal suspected of having kidney disease or kidney damage. The methods comprise contacting a sample from a mammal with one or more antibodies that specifically bind clusterin and one or more molecules that specifically bind to carbohydrate moieties of one or more clusterin isoforms (e.g., kidney specific clusterin) and that do not specifically bind other clusterin isoforms (e.g., plasma clusterin, serum clusterin, or bloodborne, non-kidney specific clusterin isoforms). One of skill in the art is aware of conditions that enable and are appropriate for formation of complexes. The complexes of kidney specific clusterin, one or more antibodies that specifically bind clusterin and one or more one or more molecules that specifically bind to carbohydrate moieties of clusterin and that do not specifically bind other clusterin isoforms that specifically bind kidney specific clusterin are detected. If the complexes are detected, then the mammal is diagnosed with kidney disease, kidney injury, or kidney damage. The amount of complexes can be determined by any methodology known in the art. A level that is higher than that formed in a control sample indicates kidney damage, kidney injury, or kidney disease. A control sample is a sample that contains either no kidney specific clusterin or kidney specific clusterin at a level observed in humans or mammals with no kidney disease, kidney injury, or kidney damage. Both types of control samples can be used in an assay. A kidney therapy or kidney therapeutic can be administered to the mammal if the mammal has kidney disease or kidney damage.

In embodiments canine kidney specific clusterin can be detected with one or more clusterin antibodies or antigen binding fragments thereof and one or more of PHA-L, WGA, sWGA, STL, LEL, PHA-E, or DSL lectins. In embodiments feline kidney specific clusterin can be detected with one or more clusterin antibodies or antigen binding fragments thereof and one or more of jacalin, ECL, LCA, RCA, PHA-E, WGA, PSA, DSL, DBA, PHA-L, SBA, or CONA lectins. In embodiments feline and canine kidney specific clusterin can be detected with one or more clusterin antibodies or antigen binding fragments thereof and one or more of WGA, sWGA, DSL, PHA-L, or PHA-E lectins. In embodiments human and feline kidney specific clusterin can be detected with one or more clusterin antibodies or antigen binding fragments thereof and one or more of PSA or DBA lectins.

Kidney damage, kidney injury, and kidney disease include, for example, acute kidney injury (AKI; functional and structural disorder or signs of renal damage including any defect from blood and urine test, or tissue imaging that is less than 3 months), a progressive or worsening acute kidney injury, an early AKI, a mild AKI, a moderate AKI, a severe AKI, chronic renal/kidney disease, diabetic nephropathy, acute tubular necrosis, acute interstitial nephritis, a glomerulonephropathy, a glomerulonephritis, proximal and distal tubular damage, a renal vasculitis, an obstruction of the renal artery, a renal ischemic injury, a tumor lysis syndrome, rhandomyolysis, a urinary tract obstruction, a prerenal azotemia, a renal vein thrombosis, a cardiorenal syndrome, a hepatorenal syndrome, a pulmonary-renal syndrome, an abdominal compartment syndrome, urinary tract infection, upper urinary tract infection, lower urinary tract infection, an injury from a nephrotoxic agent, bladder cancer, kidney cancer, urological cancer, or a contrast nephropathy.

Methods of the invention can detect kidney disease, kidney injury, and kidney damage earlier than known methods (e.g., serum creatinine assays). Methods of the invention can detect kidney disease, kidney injury, and kidney damage within about 5, 4, 3, 2, 1, or less days of onset of the detect kidney disease, kidney injury, and kidney damage.

In embodiments of the invention, the complexes are detected when an detectable label, such as an enzyme conjugate or other detectable label, which is bound to the one or more antibodies, the one or more other molecules that specifically bind carbohydrate moieties of kidney specific clusterin and that do not specifically bind carbohydrate moieties of other isoforms of clusterin (e.g., serum clusterin, plasma clusterin, or bloodborne, non-kidney specific clusterin isoforms), or both, catalyzes or provides a detectable reaction. Optionally, one or more detectable labels comprising a signal generating compound can be applied to the complex under conditions that allow formation of a detectable label complex. A detectable label complex comprises clusterin, one or more antibodies or antigen binding fragments thereof that specifically bind clusterin, one or more other molecules that specifically bind carbohydrate moieties of clusterin and that do not specifically bind carbohydrate moieties of other isoforms of clusterin, and one or more detectable label molecules. The detectable label complex is detected. Optionally, the one or more antibodies or one or more other molecules that specifically bind carbohydrate moieties of clusterin and that do not specifically bind carbohydrate moieties of other isoforms of clusterin can be labeled with a detectable label prior to the formation of a detectable label complex. The method can optionally comprise a positive or negative control.

A complex comprising clusterin, one or more antibodies that specifically bind clusterin, one or more other molecules that specifically bind carbohydrate moieties of kidney specific clusterin and that do not specifically bind carbohydrate moieties of other isoforms of clusterin (e.g. plasma clusterin, serum clusterin, or bloodborne, non-kidney specific clusterin isoforms) can also be detected using methods that do not require labels or detectable label regents. For example, surface plasmon resonance biosensors, Corning EPIC® biosensors, or colorimetric resonant reflectance biosensors can be used to detect complexes of the invention in a label-free manner.

One embodiment of the invention comprises a complex comprising one or more clusterin molecules, one or more antibodies or antigen binding fragments thereof that specifically bind clusterin, and one or more lectins. The complex can comprise one or more kidney specific clusterin molecules, one or more antibodies or antigen binding fragments that specifically bind clusterin and one or more molecules that specifically bind to carbohydrate moieties of kidney specific clusterin and do not bind to carbohydrate moieties of other clusterin isoforms (e.g. plasma clusterin, serum clusterin, or bloodborne, non-kidney specific clusterin isoforms). The complex can optionally comprise one or more detectable labels that are covalently or non-covalently bound to any component of the complex. The complex can be immobilized to a solid support.

In embodiments of the invention, one or more antibodies that specifically bind clusterin are immobilized to a solid phase or substrate. A test sample is added to the substrate. One or more other molecules that specifically bind carbohydrate moieties of kidney specific clusterin and that do not specifically bind carbohydrate moieties of other isoforms of clusterin (e.g. plasma clusterin, serum clusterin, or bloodborne, non-kidney specific clusterin isoforms) are added to the substrate before the test sample, with the test sample, or after the test sample is added to the substrate. The one or more other molecules that specifically bind carbohydrate moieties of kidney specific clusterin and that do not specifically bind carbohydrate moieties of other isoforms of clusterin can be detectably labeled. Wash steps can be performed prior to each addition to the substrate. The detectable label can be directly detected or indirectly detected via, for example, a chromophore or enzyme substrate that is added to react with the detectable label. A detectable reaction (e.g., development of color) is allowed to develop. The reaction is stopped and the detectable reaction can be quantified using, for example, a spectrophotometer. This type of assay can quantitate the amount of kidney specific clusterin in a test sample.

In embodiments of the invention, one or more other molecules that specifically bind carbohydrate moieties of kidney specific clusterin and that do not specifically bind carbohydrate moieties of other isoforms of clusterin (e.g. plasma clusterin, serum clusterin, or bloodborne, non-kidney specific clusterin isoforms) are attached to a solid phase or substrate. A test sample is added to the substrate. One or more antibodies that specifically bind kidney specific clusterin are added to the substrate before the test sample, with the test sample, or after the test sample is added to the substrate. The one or more antibodies or antigen binding fragments thereof can be detectably labeled. Wash steps can be performed prior to each addition to the substrate. The antibody label can be directly detected or indirectly detected via, for example, a chromophore or enzyme substrate that is added to the substrate to react with the detectable label. A detectable reaction (e.g., color) is allowed to develop. The detectable reaction is stopped and the reaction can be quantified using, for example, a spectrophotometer. This type of assay can quantitate the amount kidney specific clusterin in a test sample.

In embodiments of the invention, a sample is depleted of a first clusterin isoform (or multiple clusterin isoforms) in order to better detect a second clusterin isoform (or multiple other clusterin isoforms). The sample is contacted with one or more lectins that specifically bind the first clusterin isoform so that a complex of one or more lectins and one or more first clusterin isoforms are formed. In one example, DC-SIGN lectins specifically bind carbohydrate moieties of semen clusterin, but do not bind carbohydrate moieties of serum clusterin. Alternatively, a sample can be contacted with one or more molecules that specifically bind to carbohydrate moieties of the first clusterin isoforms and that do not specifically bind to carbohydrate moieties of the second clusterin isoforms so that a complex of one or more molecules that specifically bind to carbohydrate moieties of the first clusterin isoform and that do not specifically bind to carbohydrate moieties of the second clusterin isoforms and one or more first clusterin isoforms are formed. The complexes can then optionally be removed from the sample by, for example precipitation. An assay for the second clusterin can be performed using, e.g., any assay of the invention. Alternatively, any assay for the second clusterin isoform can be performed once the first clusterin isoform are depleted from the sample (e.g., contacting the sample with one or more antibodies specific for clusterin and detection of clusterin/antibody complexes). Sandwich assays using tow antibodies or direct assays using one antibody can be used.

In embodiments of the invention, a sample is depleted of non-kidney specific clusterin in order to better detect kidney specific clusterin. A sample is contacted with one or more lectins that specifically bind one or more non-kidney specific clusterin isoforms (e.g., serum or plasma clusterin isoforms) so that a complex of one or more lectins and one or more non-kidney specific clusterin isoforms are formed. WGA does not bind plasma clusterin and binds to kidney specific clusterin. Alternatively, a sample can be contacted with one or more molecules that specifically bind to carbohydrate moieties of non-kidney specific clusterin and that do not specifically bind to carbohydrate moieties of kidney specific clusterin isoforms so that a complex of one or more molecules that specifically bind to carbohydrate moieties of non-kidney specific clusterin isoforms and that do not specifically bind to carbohydrate moieties of kidney specific clusterin isoforms and one or more non-kidney specific clusterin isoforms are formed. The complexes can then be removed from the sample. An assay for kidney specific clusterin can be performed, e.g., any assay of the invention. Alternatively, any assay for kidney specific clusterin can be performed once the non-kidney specific clusterin isoforms are depleted from the sample (e.g., contacting the sample with one or more antibodies specific for clusterin and detection of clusterin/antibody complexes). Sandwich assays using two antibodies or direct assays using one antibody can be used.

Assays of the invention include, but are not limited to those based on competition, direct reaction or sandwich-type assays, including, but not limited to enzyme linked immunosorbant assay (ELISA), competitive assay, western blot, IFA, radioimmunoassay (RIA), hemagglutination assay (HA), agglutination assay, fluorescence polarization immunoassay (FPIA), and microtiter plate assays (any assay done in one or more wells of a microtiter plate). One assay of the invention comprises a reversible flow chromatographic binding assay, for example a SNAP® assay. See U.S. Pat. No. 5,726,010.

Assays can use solid phases, substrates, or supports or can be performed by immunoprecipitation or any other methods that do not utilize supports. Where a solid phase, substrate, or support is used, one or more antibodies, one or more other molecules that specifically bind carbohydrate moieties of kidney specific clusterin and that do not specifically bind carbohydrate moieties of other isoforms of clusterin, or combinations thereof, are directly or indirectly attached to a support or a substrate such as a microtiter well, magnetic bead, non-magnetic bead, column, matrix, membrane, glass, polystyrene, dextran, nylon, amylases, natural and modified celluloses, polyacrylamides, agaroses, magletite, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). In embodiments of the invention a substrate is sintered, fine particles of polyethylene, commonly known as porous polyethylene, for example, 10-15 micron porous polyethylene from Chromex Corporation (Albuquerque, NM). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing antibodies, proteins, and lectins on solid phases include ionic, hydrophobic, covalent interactions and the like.

The antibodies, lectins, or molecules that specifically bind to carbohydrate moieties of one or more clusterin isoforms (e.g., kidney specific clusterin) and that do not specifically bind to carbohydrate moieties of other clusterin isoforms (e.g. plasma clusterin, serum clusterin, or bloodborne, non-kidney specific clusterin isoforms) can be affixed to a solid support by, for example, adsorption or by covalent linkage so that the molecules retain their selective binding activity. Optionally, spacer groups can be included so that the binding site of the molecule remains accessible. The immobilized molecules can then be used to bind clusterin molecules from a sample, such as a biological sample including saliva, serum, sputum, blood, urine, feces, cerebrospinal fluid, amniotic fluid, wound exudate, or tissue.

The formation of a complex (e.g., a complex of one or more of the following: (1) clusterin, antibody or antigen binding fragment thereof, molecules that specifically bind carbohydrate moieties of one or more clusterin isoforms (e.g., kidney specific isoforms) and that do not specifically bind carbohydrate moieties of other isoforms of clusterin (e.g. plasma clusterin, serum clusterin, or bloodborne, non-kidney specific clusterin isoforms); (2) detectable label, clusterin, antibody or antigen binding fragments thereof, one or more other molecules that specifically bind carbohydrate moieties of one or more clusterin isoforms (e.g., kidney specific clusterin) and that do not specifically bind carbohydrate moieties of other isoforms of clusterin (e.g. plasma clusterin, serum clusterin, or bloodborne, non-kidney specific clusterin isoforms) can be detected by e.g., radiometric, colorimetric, fluorometric, size-separation, biosensor methods, precipitation methods, or label-free methods. Optionally, detection of a complex can be by the addition of a secondary antibody that is coupled to a detectable label. Detectable labels comprising signal generating compounds associated with a complex can be detected using the methods described above and include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Formation of the complex is indicative of the presence of one or more clusterin isoforms (e.g., kidney specific clusterin) in a test sample. The methods of the invention can indicate the amount or quantity of one or more clusterin isoforms (e.g. kidney specific clusterin) in a test sample. With many detectable labels, such as enzyme conjugates, the amount of clusterin present is proportional to the signal generated. Depending upon the type of test sample, it can be diluted with a suitable buffer reagent, concentrated, or contacted with a solid phase without any manipulation. For example, test samples can be diluted or concentrated in order to determine the presence and/or amount of clusterin.

Assays of the invention can be also used to monitor the course of amelioration of a kidney disease, kidney injury, or kidney damage. By measuring the increase or decrease of kidney specific clusterin in a test sample from a subject, it can be determined whether a particular therapeutic regiment aimed at ameliorating the disease or damage is effective.

Kits

The invention further comprises assay kits (e.g., articles of manufacture) for detecting kidney specific clusterin. A kit can comprise one or more antibodies or antigen binding fragments thereof of the invention and one or more other molecules that specifically bind carbohydrate moieties of one or more clusterin isoforms (e.g., kidney specific clusterin) and that do not specifically bind carbohydrate moieties of other isoforms of clusterin (e.g., plasma clusterin, serum clusterin, or bloodborne, non-kidney specific clusterin isoforms) and compositions for determining specific binding of the antibodies, the one or more other molecules, and clusterin in the sample. These components can comprise one or more detectable labels (i.e., the detectable labels can be immobilized to one or more of the components) or detectable labels can be provided separately. A kit can comprise a device containing one or more antibodies or antigen binding fragments thereof of the invention and one or more other molecules that specifically bind carbohydrate moieties of one or more clusterin isoforms (e.g., kidney specific isoforms) and that do not specifically bind carbohydrate moieties of other isoforms of clusterin (e.g., serum or plasma clusterin) and instructions for use of the molecules for, e.g., the identification of kidney disease, kidney injury, or kidney damage in a mammal. A kit can comprise a support with one or more antibodies or antigen binding fragments thereof or one or more other molecules that specifically bind carbohydrate moieties of one or more isoforms of clusterin (e.g. kidney specific clusterin) and that do not specifically bind carbohydrate moieties of other isoforms of clusterin (e.g., plasma or serum clusterin) or both immobilized on the support. The kit can also comprise packaging material comprising a label that indicates that the one or more one or more other molecules that specifically bind carbohydrate moieties of kidney specific clusterin and that do not specifically bind carbohydrate moieties of other isoforms of clusterin and antibodies of the kit can be used for the identification kidney disease, kidney injury, or kidney damage. Other components such as buffers, controls (e.g., positive controls like kidney specific clusterin; negative controls like plasma clusterin, serum clusterin or buffers), and the like, known to those of ordinary skill in art, can be included in such test kits. The one or more other molecules that specifically bind carbohydrate moieties of kidney specific clusterin and that do not specifically bind carbohydrate moieties of other isoforms of clusterin, antibodies, assays, and kits of the invention are useful, for example, in the diagnosis of individual cases of kidney disease, kidney injury, or kidney damage in a patient, as well as epidemiological studies of kidney disease, kidney injury, or kidney damage.

A kit can also comprise one or more lectins that specifically bind one or more non-kidney specific clusterin isoforms (e.g., serum or plasma clusterin isoforms) for formation of a complex of one or more lectins and one or more non-kidney specific clusterin isoforms. A kit can also comprise one or more molecules that specifically bind to carbohydrate moieties of non-kidney specific clusterin and that do not specifically bind to carbohydrate moieties of kidney specific clusterin isoforms, for complex formation between one or more non-kidney specific clusterin isoforms and the one or more molecules.

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

The following are provided for exemplification purposes only and are not intended to limit the scope of the invention described in broad terms above.

EXAMPLES

Example 1

Blood Contamination

Normal canine serum was spiked into negative urine (i.e., urine from healthy canines) and the amount of clusterin measured using the Commercial Clusterin EIA (Biovendor). As shown in FIG. 1A-B significant clusterin levels are measured even at 1:1000 dilution (1 μl per ml). Therefore, it is important to be able to detect kidney specific clusterin isoform while excluding any detection of serum or plasma clusterin isoform.

Example 2: Materials

Isolation of Clusterin Molecules

The sequence of canine clusterin was used to design and synthesize a vector to express a recombinant his tagged canine clusterin molecule (Life Technologies). After expression and purification of the protein, the sequence was confirmed by LC-MS. This molecule is referred to as recombinant clusterin or his-tagged recombinant clusterin herein.

Plasma clusterin was purified from pooled plasma of 30 canines by affinity chromatography. Madin-Darby canine kidney (MDCK) cell-derived clusterin (which is a kidney specific clusterin) was obtained by growing MDCK cells to confluence in 125 ml T flasks at 37° C., 7.5% $CO_2$ in 1×MEM supplemented medium with antibiotics. Supernatants were harvested and the clusterin was affinity purified over an anti-clusterin column using a AKTA chromatography system (GE Healthcare).

Kidney specific clusterin was purified by affinity chromatography from pooled urine of canines suspected of having an acute injury to the kidney.

Antibody Preparation

Polyclonal antiserum against plasma-derived clusterin was raised in rabbits. Monoclonal antibodies were generated in mice using multiple forms of clusterin as an immunogen (Immunoprecise, Inc. Vancouver, BC). The various forms included recombinant whole molecule clusterin, alpha-chain of clusterin, beta-chain of clusterin, plasma-derived clusterin, MDCK-derived clusterin, and urine-derived clusterin (which is a kidney specific clusterin).

Immunoaffinity Chromatography

Recombinant clusterin was used to immunize rabbits. The anti-clusterin IgG was purified by protein A chromatography. The anti-recombinant clusterin IgG antibodies were used to purify native plasma clusterin from a pool of canine plasma by affinity chromatography. Monoclonal antibodies were made by immunizing mice with plasma clusterin and the resulting anti-clusterin IgG antibodies were purified by protein A chromatography.

Detection Antibodies

The anti-clusterin (plasma-native) monoclonal or polyclonal antibodies were labeled with horseradish peroxide (HRP) by standard SMCC chemistry (Thermo-Pierce).

Clusterin Standard

Clusterin was purified by affinity chromatography from the culture supernatants of MDCK cell line (ATCC) or pooled canine plasma. The resulting clusterin was quantitated by LCMS. Values (mg/ml) were assigned and standard curves and controls were made.

Example 3: General Clusterin Assay Protocol

A standard curve of clusterin was prepared in assay buffer (lx PBS containing 1% BSA and 0.5% Tween® (polysorbate) 20) by serial dilution of a 500 ng/ml standard. Urine samples were diluted 1:100 in assay buffer and 100 μl was incubated for 1 hour at ambient temperature in duplicate on the plate. After 3 washes with PetChek® buffer (IDEXX Laboratories), 100 μl of anti-clusterin antibody labeled with horseradish peroxidase was incubated for 30 minutes at ambient temperature. Following 3 washes as above, 50 μl of TMB substrate (IDEXX Laboratories) was added and color was allowed to develop for 5 minutes. The colorimetric reaction was stopped by the 100 μl addition of acid (1N HCL). The plates were immediately read at 450 nm.

Clusterin Coated Plates

Microtiter plates were coated with 5 μg/ml of plasma clusterin, MDCK-derived clusterin, recombinant His-tagged clusterin, and BSA overnight at 4° C. in 0.05M carbonate buffer, pH 9.5. Following 3 washes with PBS-Tween® (polysorbate) 20 (0.1%), plates were blocked with 1% bovine serum albumin (BSA) in PBST for 2 hours. Plates were dried under vacuum for 4 hours after 3 additional washes with PBST.

Lectin Coated Plates

Biotinylated lectins (Vector Labs, Burlingame, CA) were diluted to 5 μg/ml in PBS, pH 7.4 and 100 μl and added to wells of a streptavidin coated plated (IDEXX Laboratories). After overnight binding at 4° C., plates were washed 3 times with PBST. All plates were stored, desiccated, at 4° C. until use.

Example 4: Clusterin Lectin Specificity

Clusterin coated microtiter plates were incubated for 1 hour with 1 μg/ml of biotinylated lectins in PBST. Following 3 washes with PBST, 100 μl of HRP-labeled streptavidin was incubated for 30 minutes at ambient temperature on a plate shaker. After 3 additional washes with PBST, 100 μl TMB substrate was added and incubated for 5 minutes and the reaction was stopped with 100 μl of 1N HCL. The plates were read at 450.

TABLE 2

Carbohydrate specificity of Clusterin preparations

| | Clusterin Preparation | | | | Ratio |
|---|---|---|---|---|---|
| Lectin | Plasma | MDCK | His-Tag | BSA | MDCK/Plasma |
| PHA-L | 0.3 | 2.3 | 0.1 | 0.3 | 8.8 |
| WGA | 0.5 | 2.6 | 0.1 | 0.1 | 5.5 |
| sWGA | 0.1 | 0.2 | 0.1 | 0.1 | 3.0 |
| STL | 0.1 | 0.3 | 0.1 | 0.1 | 2.2 |
| LEL | 0.7 | 1.5 | 0.1 | 0.1 | 2.2 |
| PHA-E | 1.7 | 3.6 | 0.1 | 0.4 | 2.1 |
| DSL | 1.7 | 3.2 | 0.1 | 0.3 | 1.9 |
| JACALIN | 1.5 | 2.6 | 0.2 | 0.4 | 1.7 |
| PNA | 0.1 | 0.1 | 0.1 | 0.1 | 1.5 |
| SBA | 0.1 | 0.1 | 0.1 | 0.1 | 1.4 |
| UEL | 0.1 | 0.2 | 0.1 | 0.1 | 1.4 |
| GSL-I | 0.3 | 0.3 | 0.2 | 0.1 | 1.2 |
| DBA | 0.2 | 0.2 | 0.1 | 0.1 | 1.2 |
| GSL-II | 0.1 | 0.2 | 0.1 | 0.1 | 1.2 |
| VVL | 0.3 | 0.3 | 0.1 | 0.2 | 1.1 |
| Con A | 3.5 | 3.4 | 0.1 | 0.2 | 1.0 |
| ECL | 0.6 | 0.6 | 0.2 | 0.7 | 1.0 |
| SJA | 0.3 | 0.3 | 0.1 | 0.3 | 1.0 |
| LCA | 1.8 | 1.6 | 0.1 | 0.3 | 0.9 |
| PSA | 1.5 | 1.3 | 0.2 | 0.4 | 0.8 |
| RCA | 2.9 | 2.3 | 0.2 | 0.2 | 0.8 |

Reactivity of clusterin preparations to specific lectins is shown in O.D. 450 units in Table 2. An OD>0.5 was used as a positive response to a lectin. This O.D. was chosen since binding of non-glycosylated proteins, His-tagged clusterin and BSA resulted in values ≤0.4 O.D. units. A ratio of MDCK/plasma binding was taken and ratios >2.0 were chosen for further characterization. Four (4) lectins met this criteria, PHA-E, PHA-L, WGA, and LEL. Wheat germ lectin (WGA) was selected for further characterization.

Example 5: Feasibility of Detection of Kidney Specific Clusterin

Various forms of clusterin (MDCK-derived clusterin, native plasma clusterin, and recombinant his-tagged clusterin) were serial diluted in assay buffer and detected with anti-clusterin HRP-labeled monoclonal antibody. FIG. 2 shows binding of only the MDCK-derived clusterin preparation in a dose dependent manner. The his-tagged recombinant clusterin, which has no carbohydrate, and the native plasma clusterin, which contains carbohydrate, do not bind to the lectin solid phase at any concentration tested.

Specificity of Lectin Towards Kidney Specific Clusterin

Native plasma clusterin, MDCK-derived clusterin, and urine-derived clusterin samples, were diluted to 1 μg/ml in assay buffer and detected with anti-clusterin HRP monoclonal antibodies on different lectin solid phases. Table 3 below, shows binding of only the MDCK-derived clusterin and clusterin purified from urine to the WGA solid phase. There was reduced binding to succinylated WGA (sWGA) suggesting sialic acid residues are not playing a role in binding.

TABLE 3

| | Solid Phase Clusterin Antigen | | | |
|---|---|---|---|---|
| | Native (P) | MDCK | Urine | Buffer |
| WGA | 0.08 | 1.29 | 0.98 | 0.17 |
| sWGA | 0.06 | 0.21 | 0.13 | 0.05 |
| Buffer | 0.05 | 0.05 | 0.05 | 0.05 |

Both polyclonal and monoclonal anti-clusterin antibodies are able to bind MDCK-derived clusterin bound to multiple lectin solid phases and do not bind clusterin from plasma sources because plasma-derived clusterin was not able to bind to the lectin solid phases. WGA is specific for kidney specific clusterin (MDCK-derived and urine).

Lectins were then screened for clusterin antigens that were captured on the solid phase by monoclonal or polyclonal antibodies. 3A4 monoclonal antibodies, 9H7 monoclonal antibodies, 2E2 monoclonal antibodies, 2F2 monoclonal antibodies, anti-alpha chain clusterin polyclonal antibodies, anti-beta chain clusterin polyclonal antibodies, or anti-urine clusterin polyclonal antibodies were immobilized to a solid phase. MDCK-derived or plasma-derived clusterin (1 μg/ml) was added to the solid phase along with biotinylated WGA, sWGA, Pha-L, Pha-E or buffer control. The results are show in Table 4.

TABLE 4

| Clusterin | Solid | Biotinylated Lectins or Controls | | | | |
|---|---|---|---|---|---|---|
| Antigen | Phase Ab | WGA | sWGA | Pha-L | Pha-E | Buffer |
| MDCK | 3A4 | **0.5** | 0.1 | 0.2 | **0.8** | 0.0 |
| (1 μg/ml) | 9H7 | **1.4** | 0.2 | **0.9** | **1.9** | 0.0 |
| | 2F2 | 0.1 | 0.1 | 0.1 | 0.1 | 0.0 |
| | anti-alpha | **0.4** | 0.1 | 0.3 | **1.0** | 0.1 |
| | anti-beta | **1.2** | 0.2 | **0.7** | **1.7** | 0.0 |
| | anti-urine | **0.9** | 0.1 | 0.3 | **1.4** | 0.1 |
| Plasma | 3A4 | 0.1 | 0.1 | 0.1 | 0.1 | 0.1 |
| (1 μg/ml) | 9H7 | 0.2 | 0.1 | 0.1 | 0.2 | 0.0 |
| | 2F2 | 0.2 | 0.1 | 0.1 | 0.1 | 0.0 |
| | anti-alpha | 0.1 | 0.1 | 0.1 | 0.2 | 0.1 |
| | anti-beta | 0.1 | 0.1 | 0.1 | 0.4 | 0.0 |
| | anti-urine | 0.2 | 0.1 | 0.1 | 0.5 | 0.1 |

Monoclonal antibody 9H7 and polyclonal clusterin anti-beta chain, and polyclonal clusterin anti-urine exhibit the best sensitivity. WGA, Pha-L, Pha-E specifically bound the MDCK-derived clusterin and did not specifically bind the plasma-derived clusterin.

WGA (5 μg/ml), sWGA (5 μg/ml), polyclonal anti-plasma clusterin antibody, or buffer were bound to a solid phase. Plasma-derived clusterin (1 μg/ml), MDKC-derived clusterin (1 μg/ml), urine-derived clusterin (1 μg/ml) or buffer was added. The results are shown in Table 5. Monoclonal antibody 9H7 (100 ng/ml) conjugated to the horseradish peroxidase was then added. Specific binding was detected. The MDCK-derived clusterin and urine-derived clusterin specifically bound to the immobilized WGA and was detected by the 9H7 antibody. The plasma-derived clusterin did not specifically bind to the immobilized WGA and was not detected by the 9H7 antibody. The results are shown in Table 5.

TABLE 5

| Solid Phase | Clusterin Preparation (1 μg/ml) | | | |
|---|---|---|---|---|
| 5 μg/ml | Plasma | MDKC | Urine | Buffer |
| WGA | 0.08 | 1.29 | 0.98 | 0.17 |
| sWGA | 0.06 | 0.21 | 0.13 | 0.05 |
| Poly | 0.06 | 0.06 | 0.08 | 0.06 |
| Buffer | 0.05 | 0.05 | 0.05 | 0.05 |

Freshly prepared serum was spiked into urine and the formation of sandwich immune complex was tested with a solid phase comprising immobilized WGA lectin and sWGA lectin. Lectin and kidney specific clusterin complexes were detected with HRP-conjugated 9H7 monoclonal antibody. The results are shown in Table 6. The results suggest that the complex (WGA, kidney specific clusterin, and antibody) is formed only when MDCK-derived clusterin was spiked into the urine with no significant reactivity when serum was spiked into urine between 0.1-10%. Therefore, serum clusterin is not detected by the assay.

TABLE 6

| | Normal Serum Spikes | | | | | MDKC |
|---|---|---|---|---|---|---|
| Solid Phase | 0 | 0.10% | 1.00% | 5.00% | 10.00% | (500 ng) |
| WGA | 0.05 | 0.04 | 0.05 | 0.08 | 0.12 | 0.62 |
| sWGA | 0.04 | 0.05 | 0.05 | 0.07 | 0.09 | 0.08 |

His-tagged recombinant clusterin, plasma-derived clusterin and MDCK-derived clusterin samples were reduced with DDT to separate alpha and beta chains of clusterin or remained non-reduced. In Western blots, monoclonal antibody 9H7 was demonstrated to bind to both MDCK-derived clusterin and plasma-derived clusterin. WGA lectin, however binds only to the non-reduced or reduced MDCK-derived clusterin. See Table 7. WGA did not bind to non-reduced or reduced his-tagged recombinant clusterin or non-reduced or reduced plasma-derived clusterin.

TABLE 7

| | Non-reduced | | | Reduced | | |
|---|---|---|---|---|---|---|
| | His-tagged recombinant clusterin | Plasma-derived clusterin | MDCK-derived clusterin | His-tagged recombinant clusterin | Plasma-derived clusterin | MDCK-derived clusterin |
| 9H7 | + | + | + | + | − | + |
| WGA | − | − | + | − | − | + |

Example 6 Clusterin Levels in Field Dogs with Hematuria

The urine from healthy canines was examined by UA dipstick (IDEXX Laboratories, Inc.) for the presence of blood. Kidney specific clusterin levels were measured using the Commercial Clusterin EIA according to the manufacturers' instructions (Biovendor Research and Diagnostic Products). As shown below (Table 8), healthy canines with no detectable blood in their urine had levels of clusterin within the reference range (70 ng/ml) while those having blood contamination (samples 5 to 8) had clusterin levels 10-100 times above the normal reference range. This result indicates that the presence of blood in urine may result in high clusterin measurements, leading to false positives.

TABLE 8

| Sample | Commercial Clusterin EIA | UA Dipstick Blood |
|---|---|---|
| 1 | <LOQ | Negative |
| 2 | <LOQ | Negative |
| 3 | 29 | Negative |
| 4 | <LOQ | Negative |
| 5 | 1045 | 3 |
| 6 | 1015 | 3 |
| 7 | 760 | 3 |
| 8 | 65000 | 3 |

Example 7 Specificity of the Kidney Specific Clusterin Immunoassay

A Kidney Specific Clusterin Immunoassay (KSCI) was designed using a monoclonal antibody (IgG2a, kappa) raised against canine clusterin purified from plasma and Wheat Germ Lectin (WGA). The WGA was coated onto wells of a microtiter plate. The monoclonal antibody was labeled with HRP. To illustrate the specificity of the KSCI, fresh whole blood or plasma from a healthy dog was spiked into buffer and analyzed using both the KSCI and the Commercial Clusterin EIA (Biovendor) assay.

Figure 3:
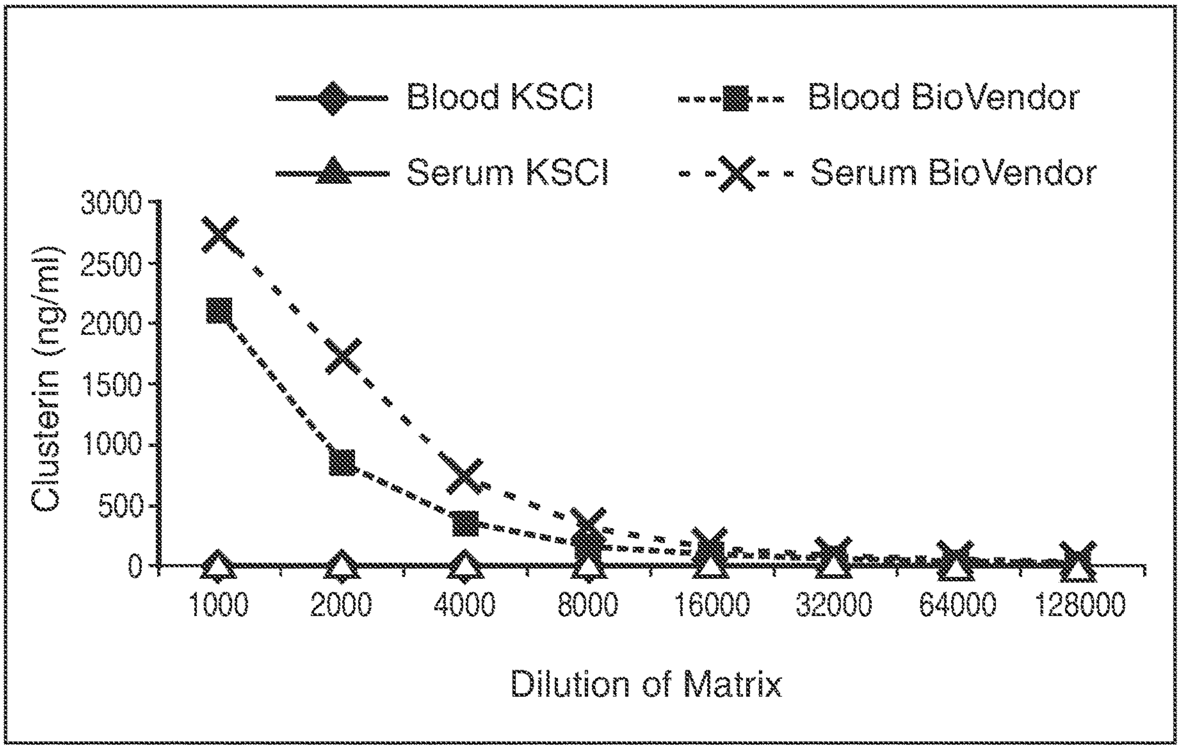
FIG. 3 shows a comparison of a commercial clusterin EIA and a Kidney Specific Clusterin Immunoassay in both whole blood and serum.

As shown in FIG. 3, clusterin was detected at high concentrations in both whole blood and serum by the Commercial Clusterin EIA but not the KSCI. Taking into consideration the fact that a high percentage of urine samples from healthy dogs and cats have blood contamination, the only way to accurately measure clusterin is to use the Kidney Specific Clusterin Immunoassay.

Example 8: Kidney Specific Clusterin in a Canine Gentamicin Model

Figure 4:
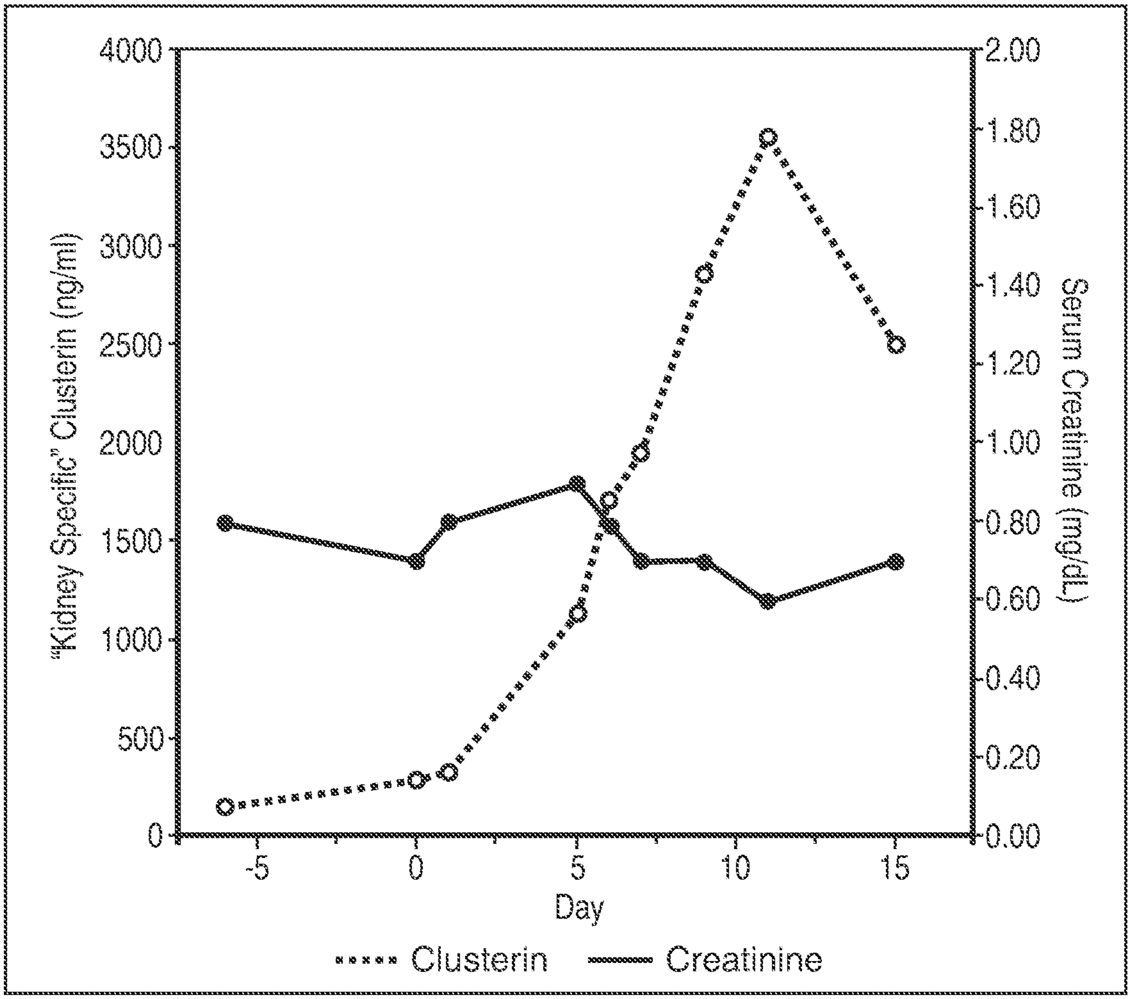
FIG. 4 shows measurement of kidney specific clusterin in urine from a canine gentamicin model.

Kidney specific clusterin was measured in urine from a canine gentamicin model (FIG. 4). In the model system, dogs were given 40 mg/kg gentamicin daily for 5 days. In this dog model, serum creatinine was essentially unchanged throughout the study while kidney specific clusterin in urine increased rapidly, reaching approximately 5 times baseline when dosing was stopped and peaking at approximately 10 times baseline at day 11. This shows that kidney specific clusterin is an earlier and more sensitive marker than serum creatinine for active kidney injury.

Example 9: Kidney Specific Clusterin in Patients with Active Kidney Injury

Figure 5:
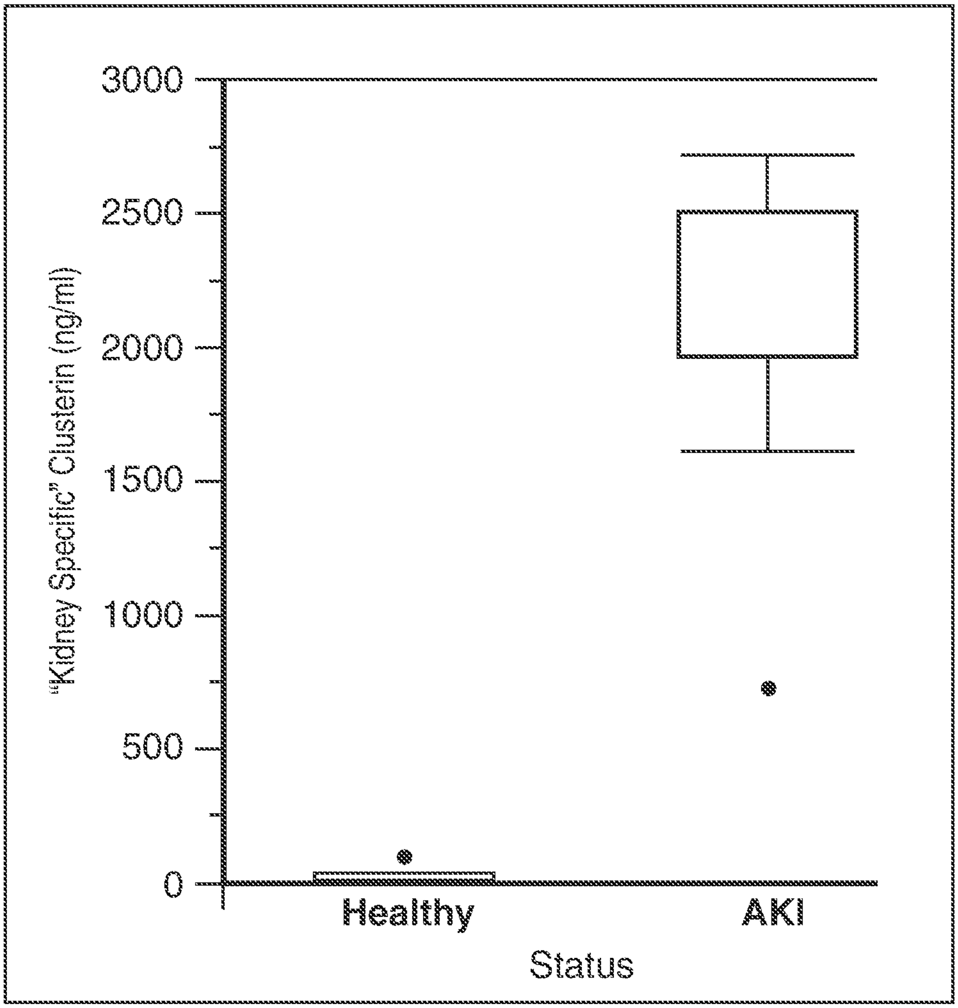
FIG. 5 shows measurement of kidney specific clusterin in urine of dogs with inflammatory or ischemic induced active kidney injury.

Kidney specific clusterin was measured in the urine of dogs presenting to a clinic with inflammatory or ischemic induced active kidney injury (FIG. 5). The data shows a clear separation in the concentration of kidney specific clusterin between healthy patients and those diagnosed with active kidney injury. In conclusion, kidney specific clusterin is a sensitive and specific marker for active kidney injury.

Figure 6:
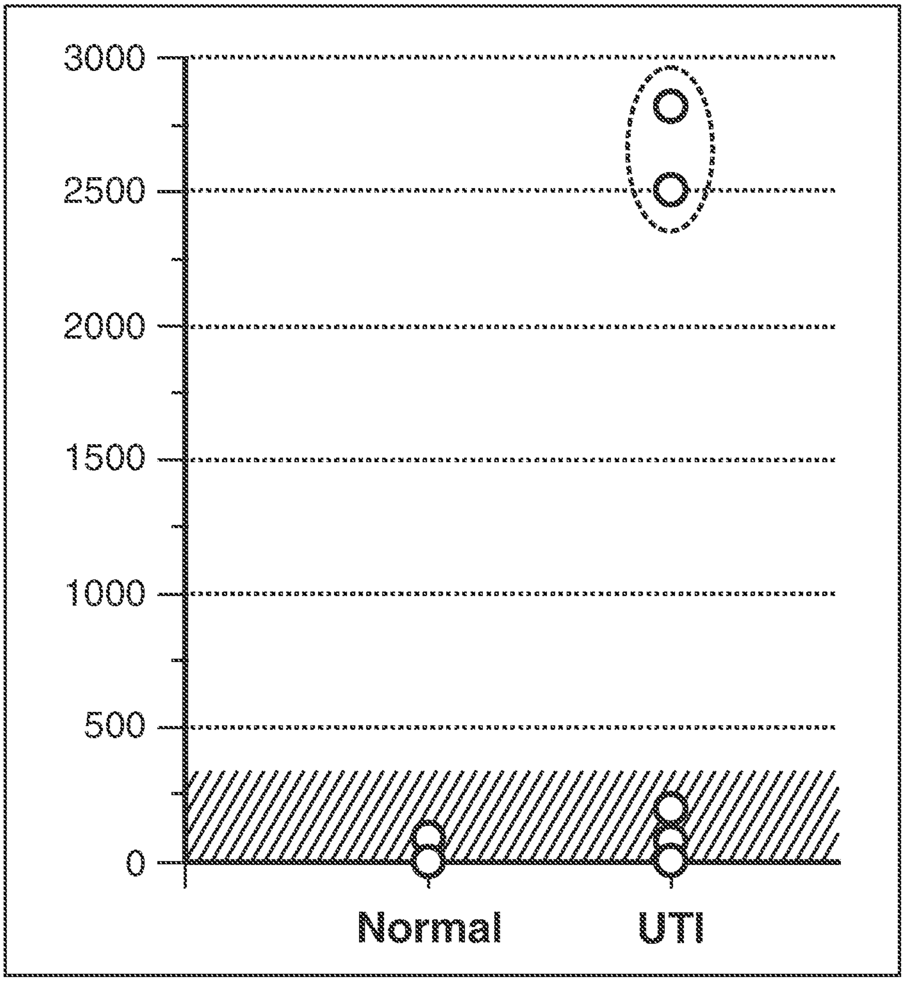
FIG. 6 shows measurement of kidney specific clusterin in patients with urinary tract infections (UTIs).

Example 10: Kidney Specific Clusterin in Patients with Urinary Tract Infections Kidney specific clusterin was measured in cats and dogs with urinary tract infections (UTIs) (FIG. 6). Kidney specific clusterin levels were dramatically increased in a subset of the UTI patients. Kidney specific clusterin is a marker for UTI.

Example 11: Kidney Specific Clusterin in Cats

Feline clusterin was isolated from feline renal CRFK cells (ATCC, Manassas, VA). Analysis of the soluble feline clusterin was done using SDS-PAGE western blotting and a lectin screening array.

Figure 7A:
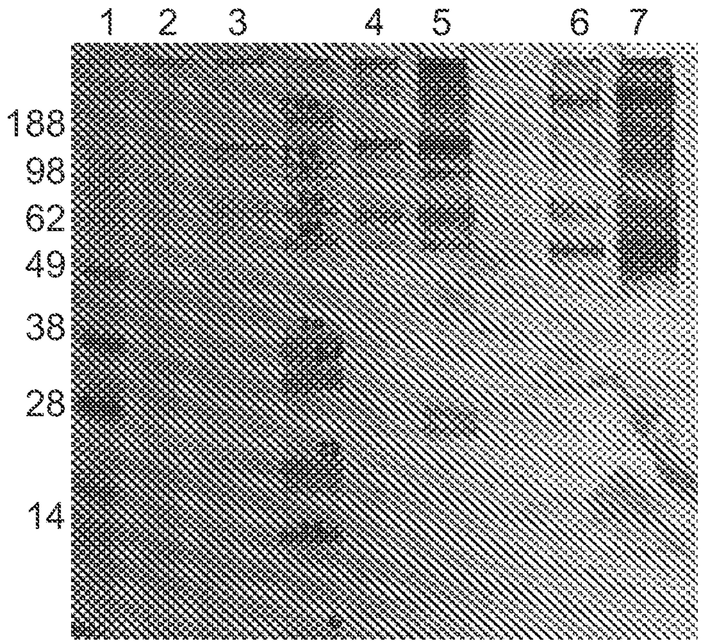
FIG. 7 shows a SDS-PAGE silver stain and western blot of feline clusterin. Panel A. Silver stain of cell culture supernatants of MDCK and CRFK cell lines from ATCC. B. Western blots showing reactivity of anti-clusterin canine monoclonal antibody with Lanes 2 and 3 MDCK (canine) clusterin, 4 and 5 Plasma (canine) clusterin, and 6 and 7 CRFK (feline) clusterin.
Figure 7B:
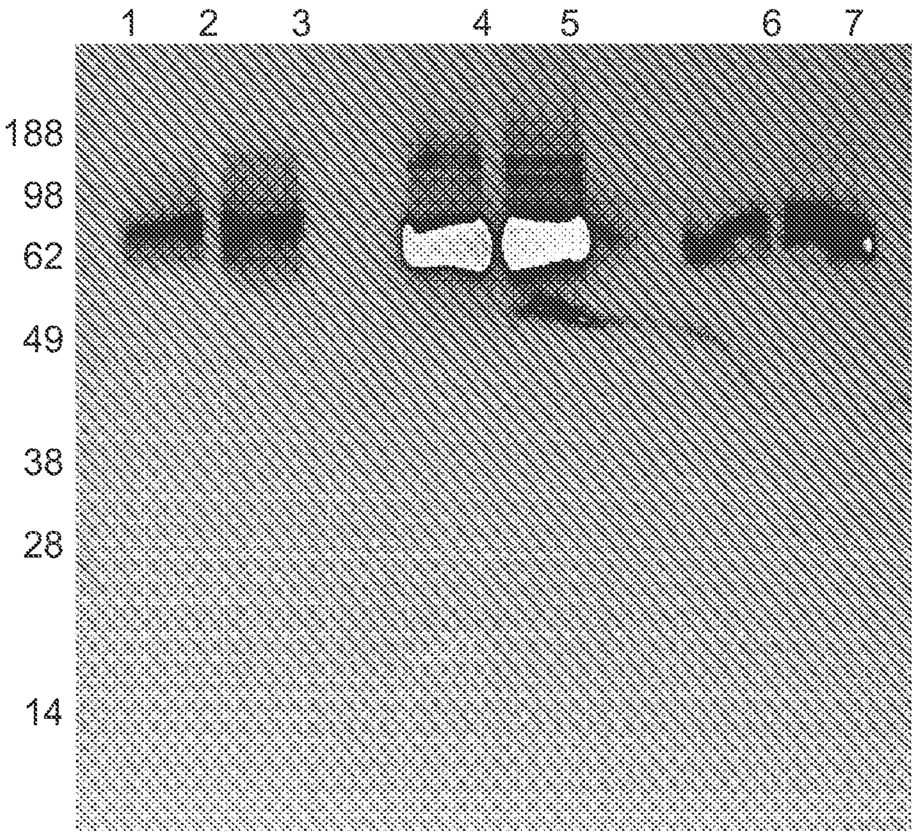

Supernatants from the canine and feline renal cell lines (MDCK and CRFK, respectively) and a clusterin preparation purified from canine plasma were run in SDS-PAGE and blotted onto nitrocellulose. The blot was probed with an anti-clusterin monoclonal antibody raised against canine clusterin. The results (FIG. 7) show that the monoclonal antibody was cross reactive with the feline clusterin produced by the CRFK. Thus, the monoclonal antibody can be used for the detection of feline renal clusterin in the two site immunoassay (ELISA) format.

Screening of Lectins to Feline Clinical Samples

Biotinylated lectins (Vector Labs) were coated at 1 μg/ml in PBST (Tween 20® (polysorbate) at 0.01%) to streptavidin coated plates overnight at 4° C. Plates were washed 3 times and feline clusterin affinity-purified from plasma (1 μg/ml) or 1:10 diluted feline clinical urine incubated for 1 hour at ambient temperature. After 3 washes, 100 μl of HRP labeled monoclonal antibody raised against canine clusterin (250 ng/ml) was added and incubated 30 minutes as above. After another three washes, 100 μl TMB was added and color developed for 5 minutes after which 100 μl 1N HCL was added to stop the reaction. Absorbance was read at 450 nm. Results are shown in Table 9.

TABLE 9

| | | Feline Sample | |
|---|---|---|---|
| Lectin Abbreviation | Lectin Source | Purified Plasma Clusterin (1 μg/ml) | Urine 1:10 dilution |
| **Jacalin** | **Jacalin** | **0.00** | **0.51** |
| GSL-I | *Griffonia* (*Bandeiraea*) *simplicifolia* I | 0.00 | 0.14 |
| **LCA** | **Lens culinaris** | **0.33** | **2.04** |
| **ECL** | **Erythina cristagalli** | **0.30** | **1.36** |
| LEL | *Lycopersicon esculentum* | −0.01 | −0.23 |
| STL | *Solanum tuberosum* | 0.00 | 0.19 |
| **RCA** | **Ricin communis** | **0.44** | **2.39** |
| VVA | *Vicia villosa* | −0.01 | −0.45 |
| GSL-II | *Griffonia* (*Bandeiraea*) *simplicifolia* II | 0.00 | 0.01 |
| SJA | *Sophora japonica* | −0.01 | 0.12 |
| **PHA-E** | **Phaseolus vulgaris** Erythroagglutinin | **0.10** | **2.53** |
| sWGA | Succinylated wheat germ | 0.01 | 0.72 |
| **WGA** | Wheat *Pisum sativum* germ | 0.05 | 2.1 |
| **PSA** | **Pisum sativum** | **1.04** | **2.62** |
| **DSL** | **Datura stratonium** | **0.36** | **2.90** |
| **DBA** | **Dolichos biflorus** | **0.08** | **1.59** |
| **PHA-L** | **Phaseolus vulgaris** Leucoagglutinin | **0.07** | **1.93** |
| UEA | *Ulex europaeus* I | −0.01 | 0.18 |
| **SBA** | **Soybean** | **0.04** | **2.06** |
| **CONA** | **Concanavlin A** | **0.65** | **3.12** |
| PNA | Peanut | 0.02 | 0.60 |

Twelve lectins (bold) were able to form a sandwich with feline clusterin and the anti-clusterin monoclonal antibody. As shown, WGA binds to feline clusterin. Thus, the KSCI assay can be used to detect clusterin in both dogs and cats.

Detection of Urinary Clusterin in Clinical Samples Using Lectin Format

Urine was collected from felines visiting a local veterinary hospital, diluted 1:100, and subjected to the KSCI assay. As shown, animals represented the range of the assay demonstrating that the KSCI assay developed for canines is cross-reactive with feline clinical samples. (<LOD=below limit of detection; >ULOQ=above upper limit of quantification). See Table 10.

TABLE 10

| Cats | Renal clusterin (ng/mls) |
|---|---|
| 1 | 31 |
| 2 | 53 |
| 3 | 144 |
| 4 | <LOD |
| 5 | <LOD |
| 6 | 208 |
| 7 | 325 |
| 8 | >ULOQ |
| 9 | 141 |
| 10 | 640 |
| 11 | <LOD |
| 12 | 125 |
| 13 | <LOD |
| 14 | 687 |
| 15 | 283 |
| 16 | 100 |
| 17 | 125 |
| 18 | 169 |
| 19 | 20 |

Example 12: Kidney Specific Clusterin in Humans

Adherent human embryonic epithelial kidney cell line HEK293, canine kidney cell line MDCK, and green monkey kidney epithelial cell line Vero (ATCC, Manassas, VA) were grown per the supplier's instructions. When cells were confluent, the cells were stressed using a nephrotoxic drug, Gentamicin 0.2 mg/ml, heated at 40° C., or treated with a combination of heat and drug. Supernatants were harvested and tested for their reactivity in a commercially available human clusterin ELISA (Biovendor). The results (Table 11) shown that the ELISA is reactive with clusterin expressed by HEK293 cells.

TABLE 11

| Specificity of Human Cell lines used for Clusterin expression | | | |
|---|---|---|---|
| Cell Line | Species/Tissue | Organ | Commercial Human Clusterin Assay Reactivity |
| MDCK | Canine epithelial | Kidney | – |
| Vero | Green Monkey epithelial | kidney | – |
| HEK293 | Human epithelial | Kidney (embryonic) | +/– |

Figure 8:
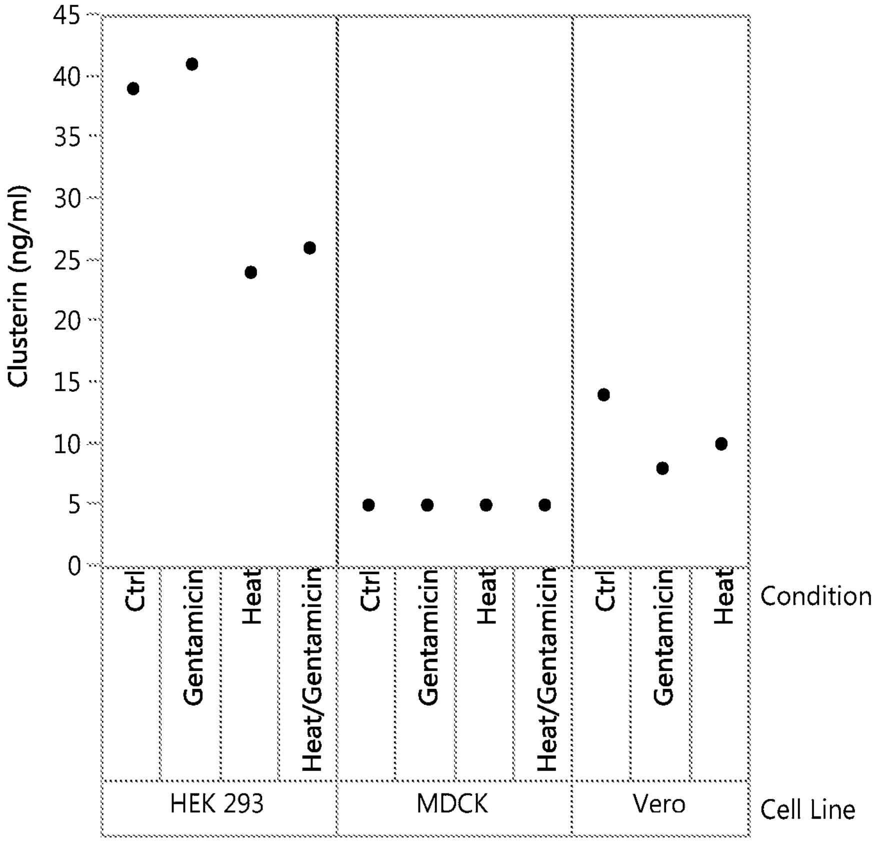
FIG. 8 shows human clusterin expression in cells grown under various conditions of stress.

Kidney cell lines were stressed with a nephrotoxic drug gentamicin 0.2 mg/ml, heat 40° C. for 24 hours, or a combination of drug (0.2 mg/ml) and heat (40° C. for 24 hrs.). The supernatants were diluted 1:100 and run in the human clusterin ELISA (Biovendor). As shown below in FIG. 8, no reactivity was seen with canine kidney cell control (MDCK). Slight reactivity was seen with the Green Monkey kidney Vero line. The human line, HEK 293 showed the strongest reactivity. This confirms that the HEK2993 cell line secreted human clusterin when grown under a variety of conditions.

Antibodies Reactive with Human Renal-Expressed Clusterin

Figure 9:
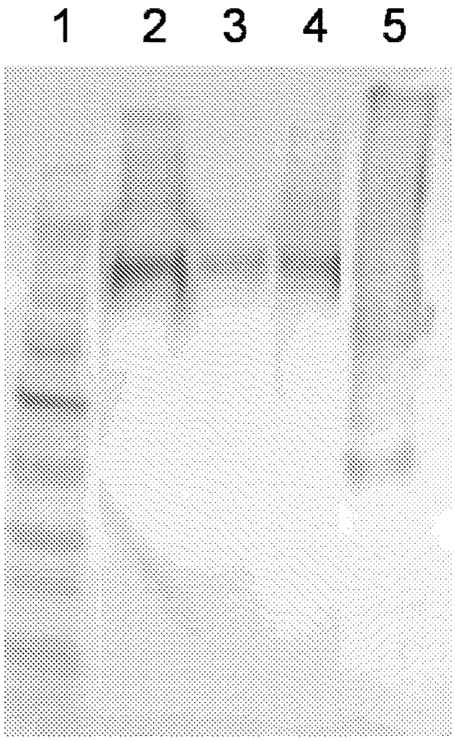
FIG. 9 shows rabbit anti-beta chain clusterin binding to clusterin from MDCK (lane 2, 4), HEK 293 cell supernatants (lane 3), and the positive control recombinant canine clusterin beta chain antigen (lane 5).

In order to develop a two site ELISA (sandwich ELISA), a library of monoclonal and polyclonal anti-canine-clusterin antibodies raised against the recombinant canine clusterin were screened to determine their binding to human clusterin. The results indicated that multiple anti-clusterin antibodies against recombinant canine clusterin, were able to bind to human clusterin. Western blot confirmation, FIG. 9, shows rabbit anti-beta chain clusterin binding to clusterin from MDCK (lane 2, 4), HEK 293 cell supernatants (lane 3), and the positive control recombinant canine clusterin beta chain antigen (lane 5).

Human Clusterin ELISA

Plates were coated with 10 μg/ml of purified anti-beta chain clusterin polyclonal antibody overnight at 4° C. The plates were washed 3 times and blocked with 0.1% BSA overnight followed by 3 final washes. The plates were dried for 2 hours under a vacuum and stored at 4° C. until use. The supernatants for the human kidney cell line and the MDCK (canine) control were diluted 1:10 with PBS and 100 μl placed in wells in duplicate. The supernatants were incubated for 1 hour at ambient temperature with shaking. After 3 washes, 100 μl of biotinylated lectins (1 μg/ml) in PBS was added and incubated for 1 hour as above. Following three additional washes, the plates were incubated for 30 minutes with streptavidin-HRP (1:5000) in PBS. After a final 3 washes the plates were developed with 100 μl TMB substrate for 5 minutes and the reaction was stopped with 100 μl 1M HCL. Absorbance was read at 450 nm. See Table 12. Two lectins (PSA, DBA) were shown to form a sandwich with human clusterin and the canine anti-beta chain polyclonal antibody.

TABLE 12

| Lectin Specificity | | | |
|---|---|---|---|
| | PSA | DBA | WGA |
| MDCK | 0.43 | 2.95 | 2.66 |
| HEK 293 | 0.38 | 1.06 | 0.12 |
| VERO | 0.50 | 1.02 | 0.06 |

We claim:

1. A method of detecting and differentiating kidney specific clusterin from non-kidney specific clusterin as an elevated level of complexes of one or more antibodies or antigen binding fragments thereof that specifically bind clusterin, one or more lectins that specifically bind carbohydrate moieties of kidney specific clusterin, and kidney specific clusterin, comprising:

contacting a urine sample from a canine, feline, or human with:

(i) the one or more antibodies or antigen binding fragments thereof that specifically bind clusterin; and (ii) one or more lectins that specifically bind carbohydrate moieties of kidney specific clusterin;

wherein, where the urine sample is a canine sample then the one or more lectins that specifically bind carbohydrate moieties of kidney specific clusterin are *Phaseolus vulgaris* leucoagglutanin (PHA-L), *Phaseolus vulgaris* agglutinin-E (PHA-E), *Datura stramonium* lectin (DSL), or jacalin lectin; where the urine sample is a human sample, the lectins are *Pisum sativum* (PSA) or

*Dolichos biflorus* (DBA); where the urine sample is a feline sample, the lectins are Jacalin, *Lens culinaris* (LCA), *Erythina cristagalli* (ECL), Ricin *communis* (RCA), *Phaseolus vulgaris* agglutinin-E (PHA-E), PSA, *Datura staronium* (DSL), DBA, *Phaseolus vulgaris* leucoagglutanin (PHA-L), soybean (SBA), or Concanavlin A (CONA); and detecting complexes of the one or more antibodies or antigen binding fragments thereof that specifically bind clusterin, the one or more lectins that specifically bind carbohydrate moieties of kidney specific clusterin, and the kidney specific clusterin wherein kidney specific clusterin is detected and differentiated from non-kidney specific clusterin.

2. The method of claim 1, wherein the one or more antibodies or antigen binding fragments thereof, the one or more lectins, or both are labeled with a detectable label.

3. The method of claim 1, wherein the antibodies specifically bind plasma clusterin, serum clusterin, recombinant clusterin, kidney specific clusterin, or MDCK-derived clusterin.

4. The method of claim 1, wherein the one or more antibodies or antigen binding fragments thereof are immobilized to a support.

5. The method of claim 4, wherein where the sample and the one or more lectins are added to the support, the one or more lectins are detectably labeled.

6. The method of claim 1, wherein the one or more lectins are immobilized to a support.

7. The method of claim 6, wherein where the sample and the one or more antibodies or antigen binding fragments thereof are added to the support, the one or more antibodies or antigen binding fragments thereof are detectably labeled.

8. The method of claim 1, wherein the detecting is completed by an enzyme-linked immunosorbent assay (ELISA), a competitive assay, an agglutination assay, a chemiluminescent assay, a bioluminescent assay, a gel electrophoresis immunoassay method, an immunohistochemistry assay, a radioimmunoassay (RIA), a label-free biosensor assay, or an immunoradiometric assay.

9. The method of claim 8, wherein the chemiluminescent assay is a chemiluminescent labeled sandwich assay.

10. The method of claim 1, further comprising diagnosing kidney injury, kidney damage, and/or kidney disease wherein elevated levels of complexes as compared to a control are detected.

11. The method of claim 1, wherein the sample is urine that is contaminated with blood.

12. A method of detection of kidney specific clusterin isoforms in the presence of plasma specific clusterin isoforms comprising contacting a sample with one or more clusterin antibodies or specific binding fragments thereof and one or more lectins that specifically bind to one or more carbohydrate moieties of kidney specific clusterin isoforms, wherein the one or more lectins are *Phaseolus vulgaris* leucoagglutanin (PHA-L), *Phaseolus vulgaris* agglutinin-E (PHA-E), *Datura stramonium* lectin (DSL), jacalin lectin, SBA lectin (soybean), *Pisum sativum* (PSA) or *Dolichos biflorus* (DBA); *Lens culinaris* (LCA), *Erythina cristagalli* (ECL), *Ricin communis* (RCA), *Datura staronium* (DSL), or Concanavlin A (CONA); and detecting complexes of the kidney specific clusterin isoforms, the one or more clusterin antibodies or specific binding fragments thereof and the one or more lectins, wherein kidney specific clusterin isoforms are detected in the presence of plasma specific clusterin isoforms.

13. A method of detecting and differentiating kidney specific clusterin from non-kidney specific clusterin as an elevated level of complexes of one or more antibodies or antigen binding fragments thereof that specifically bind clusterin, one or more lectins that specifically bind carbohydrate moieties of kidney specific clusterin, and kidney specific clusterin, comprising contacting a urine sample from a canine or feline with:

(i) the one or more antibodies or antigen binding fragments thereof that specifically bind clusterin; and (ii) the one or more lectins that specifically bind carbohydrate moieties of kidney specific clusterin, are wheat germ agglutinin (WGA), WGA1, WGA2, or WGA3, and detecting complexes of the one or more antibodies or antigen binding fragments thereof that specifically bind clusterin, the one or more lectins that specifically bind carbohydrate moieties of kidney specific clusterin, and the kidney specific clusterin, wherein kidney specific clusterin is detected and differentiated from non-kidney specific clusterin.

14. The method of claim 13, wherein the one or more antibodies or antigen binding fragments thereof, the one or more lectins, or both are labeled with a detectable label.

15. The method of claim 13, wherein the antibodies specifically bind plasma clusterin, serum clusterin, recombinant clusterin, kidney specific clusterin, or MDCK-derived clusterin.

16. The method of claim 13, wherein the one or more antibodies or antigen binding fragments thereof are immobilized to a support.

17. The method of claim 13, wherein the one or more lectins are immobilized to a support.

18. The method of claim 13, wherein the detecting is completed by an enzyme-linked immunosorbent assay (ELISA), a competitive assay, an agglutination assay, a chemiluminescent assay, a bioluminescent assay, a gel electrophoresis immunoassay method, an immunohistochemistry assay, a radioimmunoassay (RIA), a label-free biosensor assay, or an immunoradiometric assay.

19. The method of claim 13, wherein elevated levels of complexes as compared to a control are detected, then kidney injury, kidney damage, and/or kidney disease is indicated.

20. The method of claim 13, wherein the sample is urine that is contaminated with blood.

21. A method of detection of kidney specific clusterin isoforms in the presence of plasma specific clusterin isoforms comprising contacting a canine or feline sample with one or more clusterin antibodies or specific binding fragments thereof and one or more lectins that specifically bind to one or more carbohydrate moieties of kidney specific clusterin isoforms, wherein the one or more lectins are WGA, WGA1, WGA2, or WGA3, and detecting complexes of the kidney specific clusterin isoforms, the one or more clusterin antibodies or specific binding fragments thereof and the one or more lectins, wherein kidney specific clusterin isoforms are detected in the presence of plasma specific clusterin isoforms.

* * * * *